(12) United States Patent
Duffy et al.

(10) Patent No.: US 12,109,033 B1
(45) Date of Patent: Oct. 8, 2024

(54) METHODS AND APPARATUSES FOR MONITORING ECG

(71) Applicant: VivaQuant LLC, St. Paul, MN (US)

(72) Inventors: Garrett Duffy, St. Paul, MN (US); Brian Brockway, St. Paul, MN (US); Jonathan Engel, Minneapolis, MN (US); Marina Brockway, St. Paul, MN (US)

(73) Assignee: VIVAQUANT, INC., Saint Paul, MN (US)

( * ) Notice: Subject to any disclaimer, the term of this patent is extended or adjusted under 35 U.S.C. 154(b) by 409 days.

(21) Appl. No.: 16/983,691

(22) Filed: Aug. 3, 2020

Related U.S. Application Data

(60) Provisional application No. 62/882,344, filed on Aug. 2, 2019.

(51) Int. Cl.
*A61B 5/318* (2021.01)
*A61B 5/00* (2006.01)
(Continued)

(52) U.S. Cl.
CPC ............ *A61B 5/366* (2021.01); *A61B 5/0006* (2013.01); *A61B 5/282* (2021.01); *A61B 5/30* (2021.01);
(Continued)

(58) Field of Classification Search
CPC ...... A61B 5/0006; A61B 5/282; A61B 5/0245
See application file for complete search history.

(56) References Cited

U.S. PATENT DOCUMENTS

| 5,090,418 A | 2/1992 | Squires et al. |
| 5,279,283 A | 1/1994 | Dillon |

(Continued)

FOREIGN PATENT DOCUMENTS

| EP | 2664273 A1 * | 11/2013 | ........... A61B 5/0006 |
| JP | 2012 045304 A | 3/2012 | |

(Continued)

OTHER PUBLICATIONS

Widrow, et al., "Adaptive noise cancelling: principles and applications," IEEE Proc., 63(12):1692-1716 (Dec. 1975).

(Continued)

*Primary Examiner* — Michael J D'Abreu
(74) *Attorney, Agent, or Firm* — Crawford Maunu PLLC

(57) ABSTRACT

As may be implemented in accordance with one or more aspects depicted herein, an apparatus and/or method involves monitoring heart rhythm of a patient utilizing a housing having amplifying circuitry and digitizing circuitry configured to amplify and digitize ECG signals. Two or more legs protrude from the housing, each configured to provide an electrical connection from an ECG electrode to the amplifying circuitry. Computing circuitry processes the digitized ECG signals, communication circuitry communicates data corresponding to the ECG signals, and data storage circuitry stores data corresponding to the ECG signals. A charge storage circuit provides power to the circuitry, computing circuitry, and communication circuitry. The legs mechanically connect to skin electrodes and to support the weight of the housing and its contents in response to the skin electrodes being adhesively secured to skin.

28 Claims, 18 Drawing Sheets

(51) Int. Cl.
  *A61B 5/282* (2021.01)
  *A61B 5/30* (2021.01)
  *A61B 5/366* (2021.01)
(52) U.S. Cl.
  CPC .......... *A61B 5/6833* (2013.01); *A61B 5/7203* (2013.01); *A61B 2560/0214* (2013.01); *A61B 2560/0406* (2013.01)

(56) References Cited

U.S. PATENT DOCUMENTS

| | | |
|---|---|---|
| 5,313,953 A | 5/1994 | Yomtov et al. |
| 5,331,959 A | 7/1994 | Imran |
| 5,521,851 A | 5/1996 | Wei et al. |
| 5,776,073 A | 7/1998 | Garfield et al. |
| 5,792,065 A | 8/1998 | Xue et al. |
| 5,817,027 A | 10/1998 | Arand et al. |
| 5,827,195 A | 10/1998 | Lander |
| 5,987,352 A | 11/1999 | Klein et al. |
| 6,117,077 A | 9/2000 | Del Mar et al. |
| 6,389,308 B1 | 5/2002 | Shusterman |
| 6,589,189 B2 | 7/2003 | Meyerson et al. |
| 6,605,046 B1 * | 8/2003 | Del Mar ................ A61B 5/282 600/386 |
| 6,690,959 B2 | 2/2004 | Thompson |
| 6,701,170 B2 | 3/2004 | Stetson |
| 6,775,571 B1 | 8/2004 | Kroll |
| 6,821,256 B2 | 11/2004 | Ackerman et al. |
| 6,822,564 B2 | 11/2004 | Al-Ali |
| 6,856,832 B1 | 2/2005 | Matsumura et al. |
| 7,096,060 B2 | 8/2006 | Arand et al. |
| 7,099,714 B2 | 8/2006 | Houben |
| 7,115,096 B2 | 10/2006 | Siejko et al. |
| 7,236,819 B2 | 6/2007 | Brockway et al. |
| 7,272,265 B2 | 9/2007 | Kouri et al. |
| 7,376,453 B1 | 5/2008 | Diab et al. |
| 7,395,114 B2 | 7/2008 | Czygan et al. |
| 7,480,529 B2 | 1/2009 | Li |
| 7,602,985 B2 | 10/2009 | Gao et al. |
| 7,627,369 B2 | 12/2009 | Hunt |
| 7,672,717 B1 | 3/2010 | Zikov et al. |
| 7,840,259 B2 | 11/2010 | Xue et al. |
| 7,846,104 B2 | 12/2010 | MacQuarrie et al. |
| 7,966,067 B2 | 6/2011 | Rousso et al. |
| 8,086,304 B2 | 12/2011 | Brockway et al. |
| 8,201,330 B1 | 6/2012 | Rood et al. |
| 8,214,007 B2 | 7/2012 | Baker et al. |
| 8,271,073 B2 | 9/2012 | Zhang et al. |
| 8,348,852 B2 | 1/2013 | Bauer et al. |
| 8,433,395 B1 | 4/2013 | Brockway et al. |
| 8,460,189 B2 | 6/2013 | Libbus et al. |
| 8,478,389 B1 | 7/2013 | Brockway et al. |
| 8,543,195 B1 | 9/2013 | Brockway et al. |
| 8,588,908 B2 | 11/2013 | Moorman et al. |
| 8,608,984 B1 | 12/2013 | Taranekar et al. |
| 8,632,465 B1 | 1/2014 | Brockway |
| 8,755,876 B2 | 6/2014 | Chon et al. |
| 9,037,477 B2 | 5/2015 | Bardy et al. |
| 9,095,266 B1 | 8/2015 | Fu |
| 9,314,181 B2 | 4/2016 | Brockway et al. |
| 9,408,549 B2 | 8/2016 | Brockway et al. |
| 2002/0077536 A1 | 6/2002 | Diab et al. |
| 2003/0185408 A1 | 10/2003 | Causevic et al. |
| 2003/0236447 A1 | 12/2003 | Ritland |
| 2004/0111141 A1 | 6/2004 | Brabec et al. |
| 2004/0138578 A1 | 7/2004 | Pineda et al. |
| 2004/0167417 A1 | 8/2004 | Schulhauser et al. |
| 2005/0010120 A1 | 1/2005 | Jung et al. |
| 2005/0075708 A1 | 4/2005 | O'Brien et al. |
| 2005/0203604 A1 | 9/2005 | Brabec et al. |
| 2005/0234361 A1 | 10/2005 | Holland |
| 2005/0265629 A1 | 12/2005 | Fu et al. |
| 2005/0283090 A1 | 12/2005 | Wells |
| 2006/0094992 A1 | 5/2006 | Imboden et al. |
| 2007/0060815 A1 | 3/2007 | Martin et al. |
| 2007/0219453 A1 | 9/2007 | Kremliovsky et al. |
| 2007/0219455 A1 | 9/2007 | Wong et al. |
| 2007/0260151 A1 | 11/2007 | Clifford |
| 2007/0265508 A1 | 11/2007 | Sheikhzadeh-Nadjar |
| 2008/0065158 A1 | 3/2008 | Ben-Ezra et al. |
| 2008/0097280 A1 | 4/2008 | Martin et al. |
| 2008/0097537 A1 | 4/2008 | Duann et al. |
| 2008/0183093 A1 | 7/2008 | Duann et al. |
| 2008/0195169 A1 | 8/2008 | Pinter et al. |
| 2008/0200832 A1 | 8/2008 | Stone |
| 2008/0228094 A1 | 9/2008 | Audet et al. |
| 2008/0255464 A1 | 10/2008 | Vincent |
| 2008/0287770 A1 | 11/2008 | Kurzweil et al. |
| 2009/0069703 A1 | 3/2009 | Takla et al. |
| 2009/0222262 A1 | 9/2009 | Kim et al. |
| 2010/0056940 A1 | 3/2010 | Moorman et al. |
| 2010/0063438 A1 | 3/2010 | Bengtsson |
| 2010/0234916 A1 | 9/2010 | Turcott et al. |
| 2011/0046461 A1 | 2/2011 | McKenna |
| 2011/0152957 A1 | 6/2011 | Shaquer |
| 2011/0190648 A1 | 8/2011 | Gu et al. |
| 2011/0306895 A1 | 12/2011 | Nakashima et al. |
| 2012/0165691 A1 | 6/2012 | Ting et al. |
| 2012/0197144 A1 | 8/2012 | Christ et al. |
| 2012/0232417 A1 | 9/2012 | Zhang |
| 2013/0019383 A1 | 1/2013 | Korkala et al. |
| 2013/0069768 A1 | 3/2013 | Madhyastha et al. |
| 2013/0109937 A1 | 5/2013 | Banet et al. |
| 2013/0289424 A1 | 10/2013 | Brockway et al. |
| 2014/0005988 A1 | 2/2014 | Brockway |
| 2014/0135608 A1 | 5/2014 | Gazzoni et al. |
| 2014/0180597 A1 | 6/2014 | Brown |
| 2014/0364756 A1 * | 12/2014 | Brockway ............ G06K 9/0053 600/513 |

FOREIGN PATENT DOCUMENTS

| | | |
|---|---|---|
| WO | 2006/044699 A2 | 4/2006 |
| WO | 2013/043157 A2 | 3/2013 |
| WO | 2014/123512 A1 | 8/2014 |

OTHER PUBLICATIONS

Boudoulas et al., "The QT greater that QS2 syndrome: a new mortality risk indicator in coronary artery disease," American Journal of Cardiology, 50(6):1229-1235 (Dec. 1982).

Moody et al., "A noise stress test for arrhythmia detectors," Computers in Cardiology, 11:381-384 (1984).

Rao et al, "Discrete Cosine Transform: Algorithms, Advantages, Applications," San Diego, CA: Academic (1990).

J. Woods. Subband Coding, Kluwer Academic Press (1990).

Ball et al., "Dynamical Eigenfunction Decomposition of Turbulent Channel Flow," International Journal for Numerical Methods in Fluids, 12(6):585-604 (Apr. 1991).

Thakor et al., "Applications of adaptive filtering to ECG analysis: noise cancellation," IEEE Transactions on Biomedical Engineering, 38(8):785-794 (Aug. 1991).

Mallat et al., "Singularity Detection and Processing with Wavelets," IEEE Transactions on Information Technology 38:617-643 (1992).

Mallat et al., "Characterization of Signals from Multiscale Edges," IEEE Trans. Pattern Analysis and Machine Intelligence, 14(7):710-732 (Jul. 1992).

Vaidyanathan, "Multirate Systems and Filter Banks," Prentice Hall, Englewood Cliffs, 1993.

Pati et al., "Orthogonal Matching Pursuit: Recursive Function Approximation With Applications to Wavelet Decomposition," in Asilomar Conference on Signals, Systems and Computers, 1:40-44 (Nov. 1993).

Mallat et al., "Matching Pursuits with Time-Frequency Dictionaries," IEEE Transactions on Signal Processing, 41(12):3397-3415 (Dec. 1993).

Comon, "Independent component analysis, a new concept?," Signal Process. Special Issue on Higher Order Statistics, 36(3):287-314 (Apr. 1994).

(56) References Cited

OTHER PUBLICATIONS

Donoho et al., "Ideal spatial adaptation by wavelet shrinkage," Biometrika, 81(3):425-455 (1994).

Xu et al., "Wavelet Transform Domain Filters: A Spatially Selective Noise Filtration Technique," IEEE Transactions on Image Processing, 3(6):747-758 (1994).

Donoho, "Denoising by Soft-Thresholding," IEEE Trans. on Inf. Theory, 41(3):613- 627 (May 1995).

Bell et al., "An Information-Maximization Approach to Blind Separation and Blind Deconvolution," Neural Computation, 7:1129-1159. (1995).

Haugland et al., "Cutaneous Whole Nerve Recordings Used for Correction of Footdrop in Hemiplegic Man," IEEE Transactions on Rehabilitation Engineering, 3(4):207-317 (Dec. 1995).

Afonso et al., "Comparing Stress ECG Enhancement Algorithms," IEEE Engineering in Medicine and Biology, pp. 37-44 (May/Jun. 1996).

Cardoso, "Infomax and Maximum Likelihood for Source Separation," IEEE Letters on Signal Processing, 4(4):112-114 (Apr. 1997).

Hilton, "Wavelet and Wavelet Packets Compression of Electrocardiogram," IEEE Transactions on Biomedical Engineering, 44(5):394-402 (May 1997).

Hyvärinen, "New Approximations of Differential Entropy for Independent Component Analysis and Projection Pursuit," In Advances in Neural Information Processing Systems, 10:273-279, MIT Press. (1997).

Sweldens, The lifting scheme: A construction of second generation wavelets. SIAM J. Math. Anal., 29(2):511-546 (Mar. 1998).

American National Standard ANSI/AAMI EC57:1998, Testing and Reporting Performance Results of Cardiac Rhythm and ST Segment Measurement Algorithms.

Tsalaile, et al. "Blind Source Extraction of Heart Sound Signals from Lung Sound Recordings Exploiting Periodicity of the Heart Sound," ICASSP 2008 IEEE, p. 461-464 (2008).

Torres-Pereira, et. al. "A Biotelemetric Implantable Heart-Sound Rate Monitoring System," Proceedings of the XIV International Symposium on Biotelemetry, Apr. 6-11, 1997, Session 6-4, Marburg, German Abstract (1998).

Hyvärinen, "Fast and Robust Fixed-Point Algorithms for Independent Component Analysis," IEEE Transactions on Neural Networks, 10(3):626-634 (May 1999).

Cardoso, "High-Order Contrasts for Independent Component Analysis," Neural Comput., 11(1):157-192 (1999).

Chen et al., "Atomic Decomposition by Basis Pursuit," SIAM J. Scientific Computing, 20(1):33-61 (1999).

Pan et al., "Two Denoising Methods by Wavelet Transform," IEEE Trans. on SP, 47(12):3401-3406 (Dec. 1999).

Michaud et al., "Correlation waveform analysis to discriminate monomorphic ventricular tachycardia from sinus rhythm using stored electrograms from implantable defibrillators," PACE, 22(8):1146-1151 (Aug. 1999).

Mallat, "A Wavelet Tour of Signal Processing," 2nd Ed., 620 pgs., Academic Press, (Sep. 3, 1999).

Langley et al., "Comparison of three measures of QT dispersion," Conference: Computers in Cardiology, pp. 69-72 (Feb. 1999). (Abstract).

Goldberger et al., "PhysioBank, PhysioToolkit, and PhysioNet: Components of a New Research Resource for Complex Physiologic Signals," Circulation 101(23): e215-e220, Jun. 13, 2000).

Lu et al., "Wavelet Compression of ECG Signals by the Set Partitioning in Hierarchical Trees Algorithm," IEEE Transactions on Biomedical Engineering, 47(7):849-856 (Jul. 2000).

Marcellin et al., "An Overview of JPEG-2000," Proc. of IEEE Data Compression Conference, pp. 523-541 (2000).

Saul et al., "Periodic component analysis: An eigenvalue method for representing periodic structure in speech," in NIPS, [Online],, pp. 807-813 (2000). Available: http://www.cs.cmu.edu/Groups/NIPS/00papers-pub-on-web/SaulAllen.pdf.

Taswell, "The What, How, and Why of Wavelet Shrinkage Denoising," Computing in Science and Engineering, vol. 2, No. 3, pp. 12-19 (2000).

Richman et al., "Physiological time-series analysis using approximate entropy and sample entropy", Am. J. Physiol. 278:H2039-H2049 (2000).

Sayood, "Introduction to Data Compression," 2nd ed., Academic Press, Morgan Kaufmann Publishers 2000.

Malik et al., "Measurement, interpretation and clinical potential of QT dispersion," J Am Coll Cardiol, 36(6):1749-1766 (Nov. 15, 2000).

Hyvärinen et al., "Independent Component Analysis: Algorithms and Applications," Neural Networks, 13(4-5):411-430 (2000).

Mayerburg, "Sudden Cardiac Death: Exploring the Limits of Our Knowledge," Journal of Cardiovascular Electrophysiology, 12(3):369-381 (Mar. 2001). (Abstract).

Brennan et al., "Do Existing Measures of Poincare Plot Geometry Reflect Nonlinear Features of Heart Rate Variability?" IEEE Transactions on Biomedical Engineering, 48(11):1342-1347 (Nov. 2001).

Donoho et al., "Uncertainty Principles and Ideal Atomic Decomposition," IEEE Transactions on Information Theory, 47(7):2845-2862 (Nov. 2001).

Zibulevsky et al., "Blind Source Separation by Sparse Decomposition in a Signal Dictionary," Neural Computation. 13:863-882 (2001).

Oweiss et al, "MASSIT—Multiresolution Analysis of Signal Subspace Invariance Technique: a novel algorithm for blind source separation", Conference on Signals, Systems and Computers, 1:819-823 (2001).

M. Costa, A. L. Goldberger, and C.-K. Peng, Multiscale Entropy Analysis of Complex Physiologic Time Series, Phys. Rev. Lett. 89(6) (Aug. 5, 2002).

Kohler et al., "The principles of software QRS detection," IEEE Engineering in Medicine and Biology Magazine, 21(1):42-57 (2002).

G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).

T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).

D A Clunie, "Extension of an open source DICOM toolkit to support SCP-ECG waveforms," 2nd OpenECG Workshop 2004, Berlin, Germany.

J.-P Martinez, et. al., "A wavelet-based ECG delineator: Evaluation on standard databases," IEEE transactions on biomedical engineering, vol. 51, No. 4, pp. 57 (2004).

Thomsen, M. B., Verduyn, S. C., Stengl, M., Beekman, J. D., de Pater, G., van Opstal, J., et al. (2004). Increased short-term variability of repolarization predicts d-sotalolinduced torsade de pointes in dogs. Circulation, 110, 2453-2459.

Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.

Costa.et. al., "Multiscale entropy analysis of biological signals," Physical Review E 71, 021906:1-18 (2005).

M. Alghoniemy and A. Tewfik, "Reduced Complexity Bounded Error Subset Selection," IEEE Int. Conf. Acoustics, Speech and Signal Processing (ICASSP), pp. 725-728 (Mar. 2005).

S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).

Hamlin RL. Non-drug-related electrocardiogram animal models in safety pharmacology. J Pharmacol Toxicol Methods. Jul.-Aug. 2005; 52(1): 60-76.

Van der Linde et al., "A new method to calculate the beat-to-beat instability of QT duration in drug-induced long QT in anesthetized dogs," Journal of Pharmacological and Toxicological Methods 52:168-177 (2005).

(56) References Cited

OTHER PUBLICATIONS

R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).
M. Blanco-Velasco, B. Weng and KE Barner, "A New ECG Enhancement Algorithm for Stress ECG Tests," Computers in Cardiology, vol. 33, pp. 917-920 (2006).
Chen PC, Lee S, Kuo CD. Delineation of T-wave in ECG by wavelet transform using multiscale differential operator. IEEE Trans Biomed Eng. Jul. 2006;53(7):1429-33.
K. Zhang, L.-W. Chan, "An Adaptive Method for Subband Decomposition ICA", Neural Computation, vol. 18, No. 1, pp. 191-223 (2006).
R. Brychta, "Wavelet analysis of autonomic and cardiovascular signals," PhD Dissertation. Vanderbilt University (Aug. 2006).
M. Aminghafari, N. Cheze, J.-M Poggi, "Multivariate de-noising using wavelets and principal component analysis," Computational Statistics & Data Analysis, 50, pp. 2381-2398 (2006).
Aharon, M. Elad and A. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).
Chouakri S.A., et al. ECG signal smoothing based on combining wavelet denoising levels. Asian Journal of Information Technology. vol. 5, pp. 667-677. 2006.
Inan et al. "Robust Neural-Network-Based Classification of Premature Ventricular Contractions Using Wavelet Transform and Timing Interval Features," IEEE Transactions on Biomedical Engineering, 53(12-1):2507-2515 (Dec. 2006). (Abstract).
Smith, "A tutorial on Principal Components Analysis" (Feb. 26, 2002).
Ueno, et al., "Capacitive sensing of electrocardiograma potential through cloth from the dorsal surface of the body in a supine position: a preliminary study," IEEE Transactions on Biomedical Engineering, 54(4):759-766 (Apr. 2007).
K. Oweiss, A. Mason, Y. Suhail, A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).
K. Todros and J. Tabrikian, "Blind Separation of Independent Sources Using Gaussian Mixture Model," IEEE Transactions on Signal Processing, vol. 55, No. 7, pp. 3645-3658 (Jul. 2007).
R. Sameni, M. Shamsollahi, C. Jutten and G. Glifford, "A Nonlinear Bayesian Filtering Framework for ECG Denoising," IEEE Transactions on Biomedical Engineering, vol. 54, No. 12, pp. 2172-2185 (2007).
X. Li, X. Yao, J. Fox, and J. Jefferys, "Interaction Dynamics of Neuronal Oscillations Analysed Using Wavelet Transforms," Journal of Neuroscience Methods 160, pp. 178-185 (2007).
Schimpf et al., "Electromechanical coupling in patients with the short QT syndrome: Further insights into the mechanoelectrical hypothesis of the U wave," Heart Rhythm Society, 5(2): 241-245 (Feb. 2008).
Sarkar et al., "A detector for a chronic implantable atrial tachyarrhythmia monitor," IEEE Trans Biomed Eng., 55(3):1219-1224 (Mar. 2008). (Abstract).
M. Malik, K. Hnatkova, T. Novotny, G Schmidt Subject-specific profiles of QT/RR hysteresis. Am J Physiol Heart Circ Physiol 295:H2356-H2363, 2008.
Akturk et al, "Electron transport and full-band electron phonon interactions in graphene," J. of Applied Physics 103 (2008). (Abstract).
Paredes et al., "Atrial Activity Detection through a Sparse Decomposition Technique," 2:358-362, IBMEI '08 Proceedings of the 2008 International Conference on BioMedical Engineering and Informatics May 27-30, 2008, 2:358-362 (2008). (Abstract).
R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).
O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).
Li et al., "Multiresolution Subband Blind Source Separation: Models and Methods," Journal of Computers, 4(7):681-688 (Jul. 2009).
Afonso et al., Detecting ventricular fibrillation. IEEE Engineering in Medicine and Biology Magazine, vol. 14(2):152-159 (Mar./Apr. 1995).
Dash et al., "Automatic real time detection of atrial fibrillation," Ann Biomed Eng., 37(9):1701-1709. Epub Jun. 17, 2009. (Sep. 2009). (Abstract).
M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).
R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).
Piccini, et al, "Predictors of sudden cardiac death change with time after myocardial infarction: results from the VALIANT trial," European Heart Journal 2010 31(2):211-221 (Oct. 23, 2009).
J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).
Hadei et al., "A Family of Adaptive Filter Algorithms in Noise Cancellation for Speech Enhancement," International Journal of Computer and Electrical Engineering, 2(2):1793-8163 (Apr. 2010).
Allen et al.,"Honeycomb Carbon: A Review of Graphene" Chem. Rev. 110:132-145.(2010).
Attila S. Farkas et. al. Biomarkers and endogenous determinants of dofetilide-induced torsades de pointes in α1-adrenoceptor-stimulated, anaesthetized rabbits. British Journal of Pharmacology. vol. 161, Issue 7, pp. 1477-1495, Dec. 2010.
Van der Linde et al, "The Electro-Mechanical window: a risk marker for Torsade de Pointes in a canine model of drug induced arrhythmias: ElectroMechanical window and FEAB model," British Journal of Pharmacology 161:1444-1454 (2010).
Daubechies et al., "Synchrosqueezed wavelet transforms: an empirical mode decomposition-like tool," Applied and Computational Harmonic Analysis, 30(2):243-261 (Mar. 2011).
Brockway et al., "Evaluation of an algorithm for highly automated measurements of QT interval," Journal of Pharmacological and Toxicological Methods, 64(1):16-24 (Jul./Aug. 2011). (Abstract).
PhysioBank Archive Indix from PhysioNet, the research resource for complex physiologic signals. http://www.physionet.org/physiobank/database/#ecg (downloaded on Aug. 12, 2014).
MIT-BIH Arrhythmia Database from PhysioNet, the research resource for complex physiologic signals. http://www.physionet.org/physiobank/database/mitdb/ (downloaded on Aug. 12, 2014). This database is described in: Moody et al., "The impact of the MIT-BIH Arrhythmia Database" IEEE Eng in Med and Biol, 20(3):45-50 (May-Jun. 2011). (PMID: 11446209).
Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.
Kellermann, et al.,"A mobile phone based alarm system for supervising vital parameters in free moving rats," BMC Research Notes 2012, 5:119, Feb. 23, 2012.
Pan et al., "Accurate Removal of Baseline Wander in ECG Using Empirical Mode Decomposition" Proceedings of NFSI & ICFBI; pp. 177-180 (2007).
http://www.simplehelp.net/2006/09/12/how-to-set-up-outlook-2003-for-email/.
Lee, J., "Time-Varying Coherence Function for Atrial Fibrillation Detection". IEEE Transactions on Miomedical Engineering vol. 60, No. 10, Oct. 2013.
C. Li, C. Zheng, and C. Tai, "Detection of ECG characteristic points using wavelet transforms," IEEE Trans. Biomed. Eng., vol. 42, pp. 21-28, 1995.

(56) References Cited

OTHER PUBLICATIONS

V.X. Afonso, W.J. Tompkins, T.Q. Nguyen, and S. Luo, "ECG beat detection using filter banks," IEEE Trans. Biomed. Eng., vol. 46, pp. 192-202, 1999.
Z. Dokur, T. Olmez, E. Yazgan, and O.K. Ersoy, "Detection of ECG waveforms by neural networks," Med. Eng. Phys., vol. 19, No. 8, pp. 738-741, 1997.
Paul S Addison. Wavelet transforms and the ECG: a review. Physiol. Meas. 26 (2005) R155-R199.
JS. Sahambi', S.N. Tandonz5 R.K.P. Bhatt. Using Wavelet Transforms for ECG Characterization. IEEE Engineering in Medicine and Biology, Jan./Feb. 1997.
Beck et al., "An Inventory for Measuring Depression", Arch Gen Psychiatry, 4:561-571 (Jun. 1961).
Galinier et al., "Depressed low frequency power of heart rate variability as an independent predictor of sudden death in chronic heart failure", Eur. Hrt. J., 21:475-482. (2000).
Ghasemi et al., "A Semi-Automated QT Interval Measurement Based on Wavelet and Energy Analysis," http://physionet.org/challenge/2006/papers.
Pincus, "Approximate entropy as a measure of system complexity", Proc Natl Acad Sci USA, 88:2297-2301 (Mar. 1991).
Quintana et al., "Considerations in the assessment of heart rate variability in biobehavioral research", Frontiers in Physiology, 5(805):1-10 (Jul. 22, 2014).
SadAbadi et al., "A mathematical algorithm for ECG signal denoising using window analysis," Biomed Pap Med Fac Univ Palacky Olomouc Czechoslovakia., 151(1):73-8 (Jul. 2007).
Woo et al., "Patterns of beat-to-beat heart rate variability in advanced heart failure", Am Heart J., 123:704-710 (Apr. 1992).
Igarashi et al., "The Appearance of Human Skin" Technical Report: CUCS-024-05, Dept. of Comp. Sci., Columbia Univ. NY (2005).
Allen et al., "Honey Carbon: A Review of Graphene" 30 Chem. Rev. 110:132-145 (2010).
Cuiwei et al., "Detection of ECG characteristic points using wavelet transforms." Biomedical Engineering, IEEE Transactions on 42(1):21-28 (Jan. 1995). (Abstract).
Figueredo et al., "Compression of Electrocardiogram Using Neural Networks and Wavelets," Computer and Information Science Studies in Computational Intelligence, 131:27-40 (2008).
Billmang, "Heart Rate Variability? A Historical Perspective." Frontiers in Physiology (Nov. 29, 2011).
Boerma et al., "Disparity between skin perfusion and sublingual microcirculatory alterations in severe sepsis and septic shock: a prospective observational study." Intensive Care Med., 1294-1298 (2008).
Bramwell et al., The Velocity of the Pulse Wave in Man, Proceedings of the Royal Society of London: Biological Sciences, 93:298-306 (1922).
Buller et al., "Estimation of human core temperature from sequential heart rate observations," Physiological Measurement 34:781-798 (2013).
Cooke et al., "Heart rate variability and its association with mortality in prehospital trauma patients." J Trauma, 363-370 (2006).
Ezri et al., "Pulse Oximetry from the Nasal Septum." Journal of Clinical Anesthesia. 3.6:447-450 (1991).
Griffin et al., Heart rate characteristics and laboratory tests in neonatal sepsis. Pediatrics, A115(4):937-941 (2005).
Joly et al., "Temperature of the great toe as an indication of the severity of shock." Circulation, 131-8 (1969).
Morey et al., "Feasibility and Accuracy of Nasal Alar Pulse Oximetry." British Journal of Anaesthesia. 112.6:1109-1114 (2014).
Wang et al., "Optimal Depth for Nasopharyngeal Temperature Probe Positioning," Anesthesia and Analgesia. 122.5: 1434-8 (2016).

* cited by examiner

METHODS AND APPARATUSES FOR MONITORING ECG

OVERVIEW

Various aspects of the present disclosure relate to housings and configurations for wearable devices and more particularly to aspects of wearable devices for monitoring ECG, as may be useful with arrhythmia diagnosis. Aspects of the present disclosure may relate to design features of wearable devices that improve wearability and signal quality, which may improve the quality of information provided to the physician for diagnosis and monitoring of the patient.

Cardiac arrhythmias are a significant health issue. According to the Centers for Disease Control and Prevention, approximately 11 M patients in the U.S. have a heart rhythm disorder, or arrhythmia, with the most common sustained type of arrhythmia being atrial fibrillation (AF). The American Heart Association (AHA) estimates that AF affects as many as six million patients in the U.S., a condition where the upper chambers of the heart beat irregularly and blood tends to stagnate. This can result in clot formation, a dangerous condition that can lead to stroke. The National Stroke Association (NSA) estimates that one-third of AF patients have no sensation that their heart is beating abnormally. These patients are at risk of stroke, but since they don't feel any symptoms they are often not diagnosed until they have a stroke.

The number of people suffering with atrial fibrillation is increasing as our population ages. About 2% of Americans under age 65 have AF, while 9% over age 65 have AF. Good diagnostic tools are important for the effective diagnosis and treatment of AF. Early detection allows physicians to begin a customized patient treatment plan sooner, potentially preventing life threatening and costly events such as stroke or heart failure.

AF contributes to more than 750 k hospitalizations and 130 k deaths each year in the U.S. The AHA estimates that between 90 k and 120 k strokes annually are attributable to AF. Because AF can lead to blood clots that can travel to the brain, it is the leading risk factor for stroke. People with AF are about five times more likely to suffer a stroke.

Early detection and measurement of AF burden (the percentage of time a patient's heart is in AF) is important for optimizing the care of patients with AF and reducing the public health burden of treating stroke. The NSA estimates that up to 80% of strokes in people with AF can be prevented through early detection and proper treatment. The AHA/ACC/HRS Guidelines for Management of Atrial Fibrillation recommend the use ambulatory arrhythmia monitoring to help manage and evaluate the effectiveness of a patient's AF therapies which may include anticoagulation, ablation, lifestyle modification, and antiarrhythmic drugs.

Cardiac arrhythmias may be transient and can be diagnosed by having the patient wear a device that monitors the patient's ECG at the surface of the body for up to 30 days as the patient goes about their normal daily activities. Certain types of monitoring devices include: Short term Holter, long-term Holter, Event Recorder (ER), and Mobile Cardiac Telemetry (MCT). Since arrhythmias are transient, the longer the recording and the more frequently the patient wears the device, the more likely the device is to record a transient arrhythmia and make a diagnosis. In addition, noise events are common in these recordings and if noise is excessive, portions of the recording may be rendered uninterpretable. If an arrhythmia event occurs when the recording is uninterpretable, the arrhythmia may go undetected and diagnosis may be delayed. Table 1 depicts information for certain types of monitors.

TABLE 1

Features of recordings provided for ambulatory arrhythmia monitoring.

| Monitor Type | Recording Duration | AF Burden | Heart Rate Trend | Diag. Yield | Arrhythmia Statistics Reported | Requires 24/7 Coverage |
|---|---|---|---|---|---|---|
| Short-term Holter | 24-48 Hours | No | No | 24% | Yes | No |
| Long-term Holter | 3-21 Days | Yes | Yes | NA | Yes | No |
| Event Recorder (ER) | Up to 30 Days | No | No | 23% | No | Yes |
| Mobile Cardiac Telemetry (MCT) | Up to 30 Days | Yes | Yes | 61% | Yes | Yes |

Data show that 39% of patients that undergo a monitoring session fail to achieve a diagnosis, even when the best type of monitoring is performed [Tsang and Mohan, Medical Devices: Evidence and Research, 2014:7]. Part of the reason for this unsatisfactory performance is that patients remove the device because it is uncomfortable to wear or difficult to use.

Some devices require a very aggressive skin preparation procedure involving an abrasive pad, followed by an isopropyl alcohol rub of the abraded area, followed by "massaging" the electrode into the skin surface for 2 minutes. This prep procedure can produce discomfort and, in some cases, pain. Despite the extensive prep procedure, devices may fall off the skin within 5-7 days, especially following a workout or exposure to summer weather that induces heavy sweating. Because some devices use custom electrodes with an integrated patch, the cost of replacing the device is significant. The same device placed back on the skin will often not adhere.

SUMMARY

Various aspects of the present disclosure are directed to devices for ambulatory monitoring of arrhythmias in a manner that addresses challenges and limitations including those discussed above.

In accordance with various example embodiments, a wearable device with dimensions approximately 40×55×15 mm is positioned on or near the surface of the body. The wearable device includes legs extending from the lateral surfaces of the device for connection to one or more skin electrode patches, each patch containing one or more electrodes for sensing electrical activity at the surface of the body.

In one embodiment, four legs extend from the device, with each leg having a foot enclosing a snap for connection to an electrode for sensing biopotentials. Legs are positioned to provide a minimum center-to-center distance between electrodes that represent a sensing vector of at least 6 cm. In an alternate embodiment the distance between the electrodes that represent a sensing vector is at least 4 cm.

To reduce stress at the tissue electrode interface during patient movement and skin stretching, the legs are designed to flex to allow the relative position of the electrodes to move slightly as the patient moves about. Flex can be in the horizontal plane, vertical plane, or both.

The above summary is not intended to describe each embodiment or every implementation of the present disclosure. The figures and detailed description that follow more particularly exemplify various embodiments.

BRIEF DESCRIPTION OF THE DRAWINGS

Aspects of the disclosure may be more completely understood in consideration of the following detailed description of various embodiments in connection with the accompanying drawings, in which.

Figure 1:
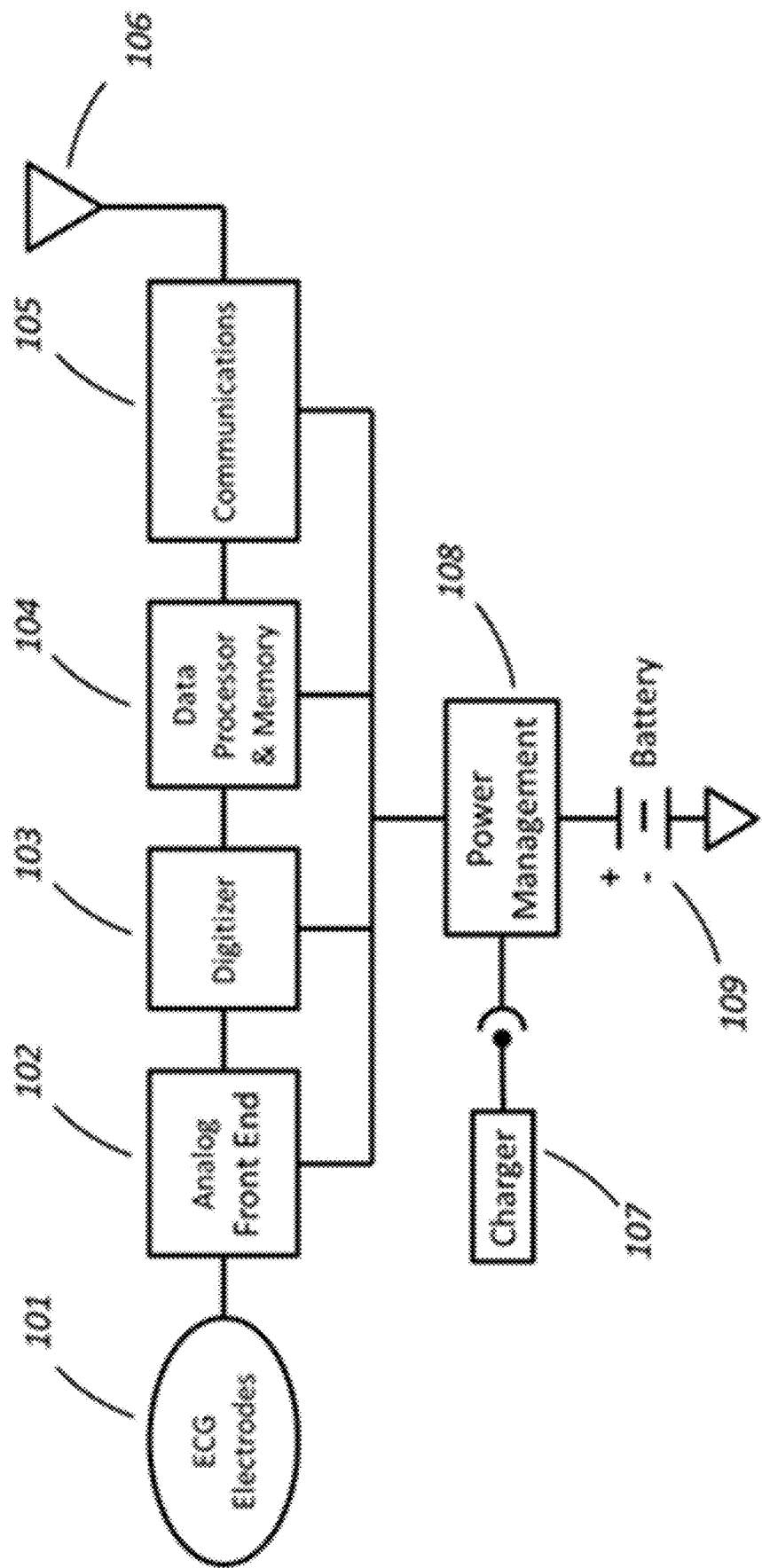
FIG. 1 illustrates a system block diagram, in accordance with one or more embodiments.

While the embodiments herein are amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION

Various example embodiments of the present disclosure relate to systems that acquire and process physiological signals used for monitoring vital signs for diagnostic or monitoring purposes. While the present disclosure is not necessarily limited to this application, various aspects of the disclosure may be appreciated through a discussion of examples using this context.

In one embodiment, the subject device is used to monitor electrocardiogram (ECG) of a patient to provide diagnostic information such as arrhythmias. The device can be worn on the surface of the body and includes a housing that contains electronic circuits to acquire, process and communicate the ECG and a battery to power the electronic circuits. The housing may be water-tight to allow the device to be worn in the shower.

As may be implemented in accordance with one or more embodiments, an apparatus for monitoring heart rhythm of a patient includes a housing and, within the housing, amplifying circuitry and digitizing circuitry configured to amplify and digitize ECG signals. The apparatus further includes two or more legs protruding from the housing, each configured to provide an electrical connection from an ECG electrode to the amplifying circuitry. As may also be implemented in the housing, the apparatus includes computing circuitry, communication circuitry, data storage circuitry and a charge storage circuit. The computing circuitry is configured for processing the digitized ECG signals, the communication circuitry (e.g., wired and/or wireless) is configured for communicating data corresponding to the ECG signals, and the data storage circuitry stores data corresponding to the ECG signals. The charge storage circuit provides power to the circuitry, computing circuitry, and communication circuitry. The legs are configured to mechanically connect to skin electrodes and to support the weight of the housing and its contents in response to the skin electrodes being adhesively secured to skin.

In connection with such approaches, it has been recognized/discovered that, by utilizing legs for connecting the housing to the electrodes, electrode motion noise may be reduced such that, when utilized with communication circuitry for processing the digitized ECG signals, desirable signals may be obtained and communicated at relatively low power. In some embodiments, the two or more legs are configured and arranged with the housing and the electrodes to reduce electrode motion noise by mechanically absorbing shock relative to the electrodes. For instance, legs having a spring constant that allows movement of the housing relative to the electrodes and absorbs forces, torque or other shock may reduce noise 4-5 times. In certain implementations, the legs include a spring constant between 5 N/m and 20 N/m in an X-Y plane along which the legs extend from the housing (e.g., along a plane of the surface of the skin to which the electrodes are attached), and between 10 N/m and 25 N/m along a Z axis perpendicular to the X-Y plane (e.g., extending toward the patient's skin).

It has also been recognized/discovered that such approaches facilitate the use of integrated cellular or other wireless modems within the housing, utilizing the reduced electrode motion noise to, in turn, limit RF energy absorption under FCC specific absorption requirements (e.g., 1.6 W/kg, averaged over any 1 gram of tissue). This solves challenges including those characterized above, and which may otherwise force such a wearable apparatus to be place at least 6 cm from a patient's skin. As such, various embodiments are directed to such an apparatus with cellular communication circuitry within the housing.

The legs may be implemented in a variety of manners. For instance, the legs may be flexible in the X-Y plane, flexible in the Z axis, exhibit a curved or S-shaped shape, and may be fabricated of a material that renders them flexible such as one or more of Thermoplastic Elastomers (TPE), Thermoplastic Vulcanizates (TPV), Thermoplastic Urethane (TPU), Flexible Polyvinyl Chloride (PVC), and silicone rubber. In some embodiments, the one or more of the legs include an insert with a specified spring constant to control the flexibility of a leg. In some embodiments, the legs are configured and arranged with a stiffness and flexibility that, with a weight of the apparatus, limits torque applied to the adhesively secured skin electrodes to below a threshold amount of torque that would counter the adhesive and lift one of the electrodes off the patient's skin. The stiffness and flexibility may further facilitate movement of the housing relative to the patient's skin.

In some implementations, the computing circuitry further reduces power consumption for effecting communications by denoising the ECG signals and effecting data compression. For instance, the volume of data (after denoising/compression) may be reduced such that radiated radio frequency energy required for communication of the data is below FCC specific adsorption limits as characterized above when the housing is in direct contact with the patient's skin. Accordingly, power required for monitoring heart rhythm of a patient may be sufficiently low such that amplifying circuitry, digitizing circuitry, computing circuitry, cellular communication circuitry, data storage circuitry, and charge storage circuitry can be packaged within a housing having a volume of less than 33 cc. Such an apparatus may further be implemented at low power, with a battery life greater than 3 days.

In some implementations, the apparatus also includes the skin electrodes. The skin electrodes may include a single sensing surface configured to contact the skin for obtaining the ECG signals. Further, four skin electrodes may be arranged in two arrays, with each array including two sensing surfaces. The skin electrodes may be configured in an array with each electrode connected to a one of the legs.

Another embodiment is directed to an apparatus comprising electrodes configured to attach to the skin of a patient and to obtain ECG signals from the patient, and a housing including circuitry to digitize and remove noise from ECG signals obtained from the electrodes and to transmit signals corresponding to the ECG signals, and a power source to power the circuitry. The apparatus further includes legs connecting the housing to the electrodes and being configured and arranged with the housing and electrodes to suspend the housing relative to the skin to which the electrodes are attached and to, with the housing suspended, maintain the electrodes in contact with the skin and obtaining the ECG signals via the electrodes.

In some implementations, the legs exhibit a stiffness that allows movement of the electrodes relative to each other while maintaining electrical contact between the electrodes and the skin that is sufficient for obtaining the ECG signals. The legs may be configured and arranged with the electrodes to suspend the housing relative to the skin with the housing adjacent to and in contact with the patient's chest, while allowing movement of the housing relative to the patient's chest. In connection with such approaches, it has been recognized/discovered that use of legs for allowing movement and absorbing force, torque and/or other shock facilitates a reduction in electrode motion noise. This reduction allows lower power operation and smaller/lighter componentry (e.g., the housing may weigh less than 47 grams), the latter of which further facilitates a reduction in noise due to lower forces/torques.

The circuitry in the housing may further remove the noise from the ECG signals. In one implementation, noise is removed by identifying a location of a QRS complex of a cardiac cycle in the ECG signals, identifying a first time window in the cardiac cycle that includes the QRS complex and identifying a second time window in the cardiac cycle that does not include the QRS complex. A band of frequencies is then removed from the second time window. In another implementation, noise is removed by decomposing the signal into subcomponents, identifying a location of the QRS complex of a cardiac cycle in the ECG signal, identifying a time window in the cardiac cycle that includes the QRS complex, and identifying a time window in the cardiac cycle that does not include the QRS complex. For each of the time windows, target ones of the subcomponents in the time window are identified as subcomponents that contain more energy that is within a band of frequencies characteristic of a desired ECG signal in the time window than energy that is outside the band of frequencies characteristic of the desired ECG signal. A denoised signal is then reconstructed using at least two of the identified target subcomponents.

Various embodiments are directed to apparatuses and methods for monitoring arrhythmias, utilizing one or more of the following attributes:

Long battery life. The need to recharge or replace batteries is often difficult for elderly. Longer battery life makes it easier for elderly patients to comply with monitoring.
  One-piece device with on-board cellular communication
  Accurate on-board arrhythmia detection for long battery life and more robust cellular communication
  High-clarity ECGs for easy and dense interpretation
  Small size and light weight. May requires no special support apparatus such as a lanyard or belt.
  Comfortable for the patient to wear for long periods of time. The patient may forget the device is present.
  Device can be worn at all times, including in the shower, while swimming, and while exercising
  In some implementations, does not use lead wires to connect to electrodes. Lead wires can be cumbersome when connecting the device to the patient and can be uncomfortable for some patients.
  If the device falls off (e.g. due to excessive sweat) the skin, it can be reattached to the patient using inexpensive electrodes.
  If the patient's skin reacts to electrodes and the area under the electrodes becomes itchy, the patient can move the device to a new location on the chest without the need for expensive electrodes.

Various embodiments address needs such as by providing an apparatus that:
  attaches to and is supported by the skin without the use of "lead wires"
  is small and comfortable to wear
  can be easily reattached to the skin if it falls off using inexpensive commercially available electrodes provides a stable interface between the skin and sensing electrode. Patient movements will not unduly displace the electrode on the skin and hence significant movement artifact is avoided.

provides real-time monitoring using a small single-piece device without lead wires.

allows electrodes to move relative to each other as the patient's body moves.

does not significantly restrict electrode movement as the patient goes about normal daily activities. This attribute improves signal quality by reducing stress at the tissue electrode interface and improves patient comfort resulting in better patient compliance.

Various embodiments are directed to one or more aspects of underlying U.S. Provisional Patent Application Ser. No. 62/882,344, filed on Aug. 2, 2019 and to which the instant application claims benefit, and which is fully incorporated by reference herein.

Referring to the figures, beginning with FIG. 1, the ECG electrodes 101 sense an electrical signal from the body. Analog front end (AFE) 102 amplifies and filters the sensed electrical signal and digitizer 103 converts the analog signal to digital values. Data processor and memory 104 process the digital values, extract information such as arrhythmias and heart rate, and save the information in memory. Data processor 104 also communicates the digitized and processed information to communications module 105 is an electronic circuit which communicates the information wirelessly via antenna 106. In one embodiment, the wireless link is a cellular network. In another embodiment, the wireless link is a short range connection such as BlueTooth. In another embodiment, the processed data are saved in memory and later retrieved from memory using a wired link such as a USB communication link.

The device includes battery 109, which may be a rechargeable battery. The battery is charged using either a plug-in charger or, alternately, using a wireless charger. Power management circuit 108 manages charging of the battery and regulation of the battery voltage used to power the electronic circuits and processor.

In various implementations, the data processor 104 removes noise from the digitized ECG signals and compresses the data volume in a manner that facilitates communicating the signals or another communication based on the signals, utilizing a lower duty transmitter duty cycle and reduced power. It has been recognized/discovered that, by reducing noise such signals, compression can be rendered more efficient. This can facilitate using a cellular modem designed for low-data volume IoT applications. The IoT modem can be built into the system shown in FIG. 1 and may be combined into a housing worn against human skin along with the other elements of FIG. 1. In some embodiments, this approach results in a lower level of radio frequency radiation allowing the device to be safely worn directly on the skin. This embodiment may, for example, allow the device to meet FCC specific adsorption limits when placed directly on the skin.

It has further been recognized/discovered that, by reducing power needed for processing and communicating the signals, the battery can also be reduced in size and weight, facilitating wearing of such a housing. Further, by utilizing legs with flexibility characterized herein to couple the signal from the electrodes to the housing, patient comfort and signal quality can both be maintained. The leg design described herein provides good quality ECG signals and patient comfort by limiting the generation of torque in the legs to level below that which would tend to twist or induce tension in the skin. Such an apparatus can be worn and utilized in a manner that addresses various challenges as noted hereinabove. For general information regarding denoising of signals, and for specific information regarding approaches to denoising that may be implemented in accordance with one of more embodiments herein, reference may be made to U.S. Pat. Nos. 8,632,465; 10,028,706; 10,231, 638; and to the underlying patent documents referenced therein, all of which are fully incorporated by reference.

Figure 2:
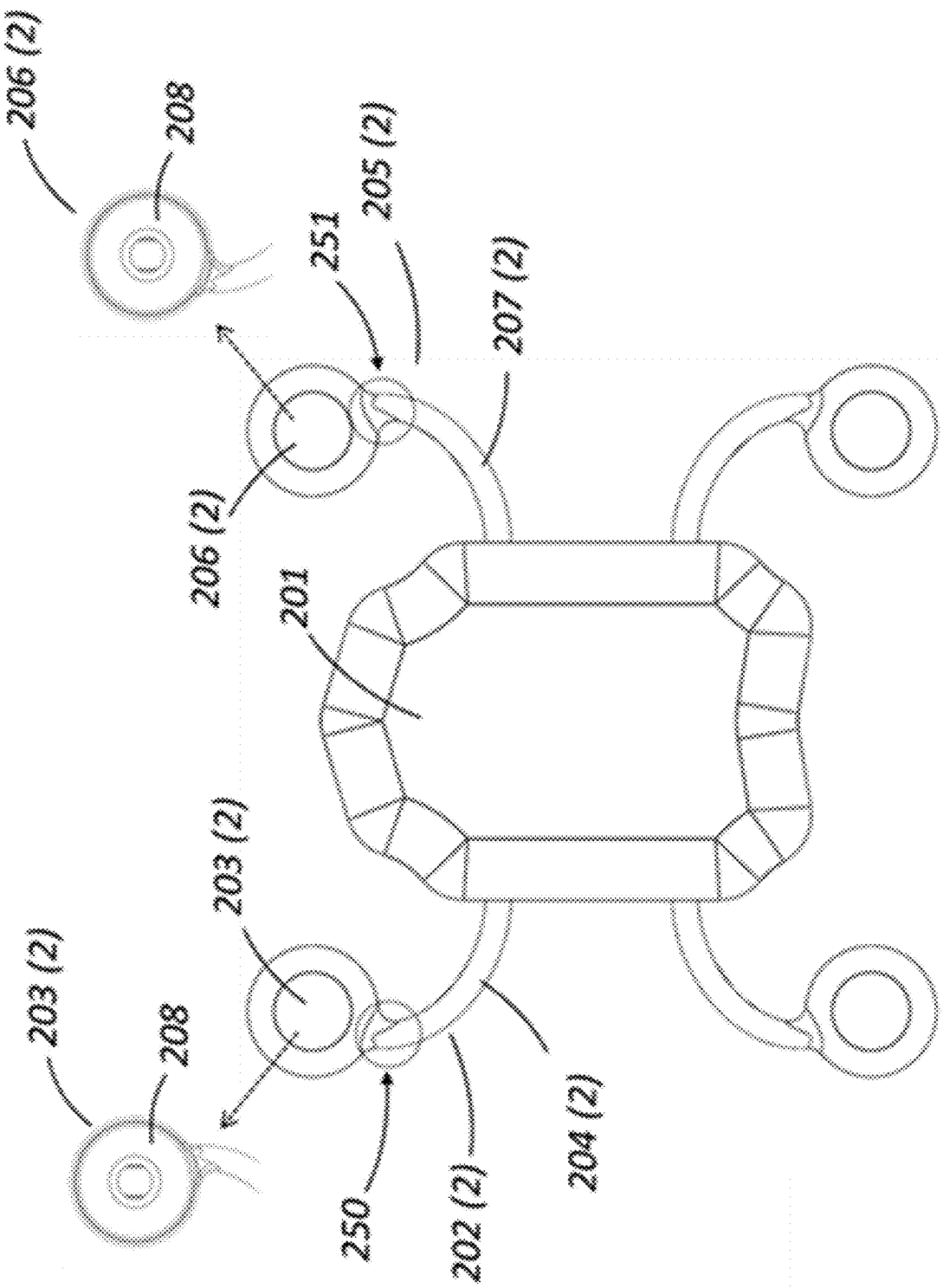
FIG. 2 illustrates a device with four spline-shaped legs, in accordance with one or more embodiments.
Figure 3:
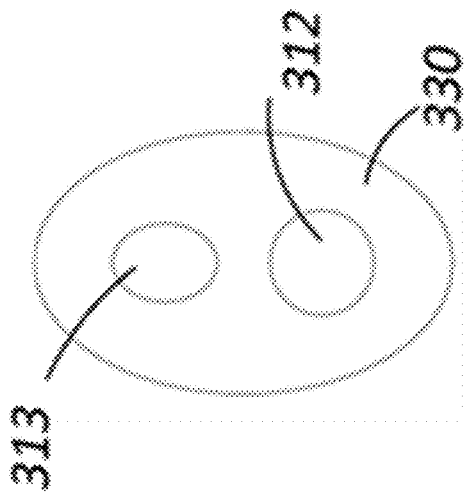
FIG. 3 illustrates three designs for the cross section of the legs, in accordance with one or more embodiments.
Figure 3:
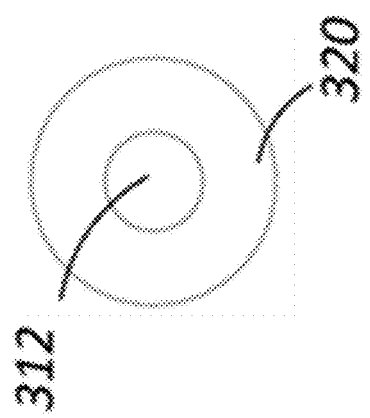
Figure 3:
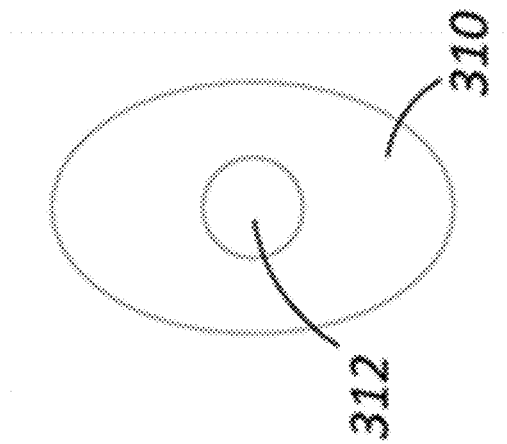

One apparatus or system type embodiment includes a housing with legs extending from the perimeter. Referring to FIGS. 2, 3, and 8, one embodiment of the device has four flexible legs 202, 205 protruding from housing 201. Each leg 202, 205 contains flexible portion 204, 207 protruding from the housing 201, and feet 203, 206 which are positioned at the end of the flexible portion 204, 207. Each foot contains a female button snap 208. The female button snap 208 is molded within each foot 203, 206 and allows the device 201 to be connected to standard commercially available ECG electrodes 805 adhesively attached to the skin surface of the patient. An example of electrodes 805 is 3M (St. Paul, MN) Model 2259. When attached to standard electrodes on a body, electrical signals of the heart are passed from the surface through the snap 208, to wires molded within the leg 312, and into an analog front end 102 contained within the device housing 201.

In one embodiment, legs 202, 205 are flexible to allow electrodes 805 to move relative to each other. Legs 202 and 205 are similar in design, with the exception that the curvature is clockwise in 202 and counter clockwise in 205. In this embodiment legs 202, 205 are curved. The curvature of the legs is represented by a spline function described as $y=a+bx+cx^2$. The degree of flexibility in the flexible portion 204 and 207 is chosen by a tradeoff of two competing design goals: a) maintain a sufficiently high degree of flexibility to maintain an acceptable level of stress on the electrode-tissue interface as the electrodes move relative to each other, and b) maintain a sufficiently low degree of flexibility to maintain stability of housing 201 when attached to electrodes 805.

The flexibility of the flexible portion 204 and 207 can be represented by the spring constant, k, of the legs. The spring constant is dependent upon the shape and length of the flexible portion 204 and 207 of legs 202 and 205, the mechanical properties of the material, and the cross-sectional design. Device housing 201 is floating and only supported by the connection of the feet 203, 206 to electrodes adhesively attached to the skin. Hence, if legs 202, 205 are too flexible, the device may not remain in a stable position on the patient's body. In one embodiment, legs 202 and 205 provide a lower spring constant (greater flexibility) in the x and y directions, while providing a larger spring constant (less flexibility) in the z direction. This may allow flexibility with certain movements of the body (i.e. lifting arm, swimming) that may cause the electrodes to move relative to each other while also assuring that device 201 maintains its position with other movements (i.e. jogging, leaning over). Designing the cross section of the leg 202, 205 to restrict flexibility in the z direction may help maintain the positioning of the device housing 201 on the body.

In one embodiment the position of feet 203, 206 on each leg 202, 205 can be modified to position them closer or further away from the device housing 201. Altering this distance change the distance between electrodes. Changing distance between electrodes impacts the amplitude of the sensed ECG signal with larger distance increasing the amplitude and smaller distance decreasing the amplitude. Distance and spring constant can be altered by changing the shape of the legs flexible portion 204, 207.

In another embodiment, the legs 202, 207 of the device include a feature 250, 251 which allows feet 203, 206 to flex in the z direction. This allows the foot, snap, and electrode to adjust to different body contours, so that the electrode may remain parallel with the skin surface without creating stress in the legs which attach it to the housing. This feature may allow device 201 to move in the Z direction with a change in the position electrode (e.g. a single electrode changes position relative to a plane which includes the other electrodes) but will allow a change in the z-axis of one electrode relative to the other electrodes to reduce stress on the tissue electrode interface.

In another embodiment, this feature 250, 251 could be substituted by replacing the snap 208 within each foot 203, 206 with a modified snap which allows the electrode to rotate a certain amount. This interaction between the snap and electrode could function similar to a ball-and-socket joint that allows the electrode to remain parallel with the surface of the skin while not creating stress in the legs which attach to the housing.

Three example cross section designs of the flexible portions 204 and 207 of legs 202 and 205 are illustrated in FIGS. 3a, 3b, and 3c. Although these three embodiments include 3 design features, other possibilities exist for the leg cross section. Embodiments exist that combine features from each design in order to optimize performance of the legs 202, 205. All three designs 3a, 3b, 3c contain a wire 312 molded within a flexible material 310, 320, 330. In one embodiment, (see FIG. 3a) flexible material 310 is molded around the wire 312 into a cross section that is larger in the z dimension vs. the xy dimension, creating an oval cross-section. The wire 312 provides an electrical connection between the snap 208 and AFE 102. The oval cross section 310 provides a larger spring constant in the z direction vs. the x direction. This stiffness is the z direction may be useful to maintain position of device 201 near the skin and resist forces, such as gravity, that work to pull the device away from the body surface. The design in FIG. 3b molds the flexible material 320 around the wire 312 into a circular cross section which is uniform in the z and x directions. This cross section may be useful to maintain a consistent spring constant in both x and y directions. In another embodiment of legs 202 and 205, flexible material 330 is provided in an oval cross section and includes wire 312 and insert 313. In one embodiment insert 313 includes a wire, polymer, or other material with a specified spring constant molded within the leg and may be useful in controlling the spring constant of legs 202 and 205. Insert 313 may be useful by providing an additional design feature that can be used to achieve a desired spring constant.

Figure 4:
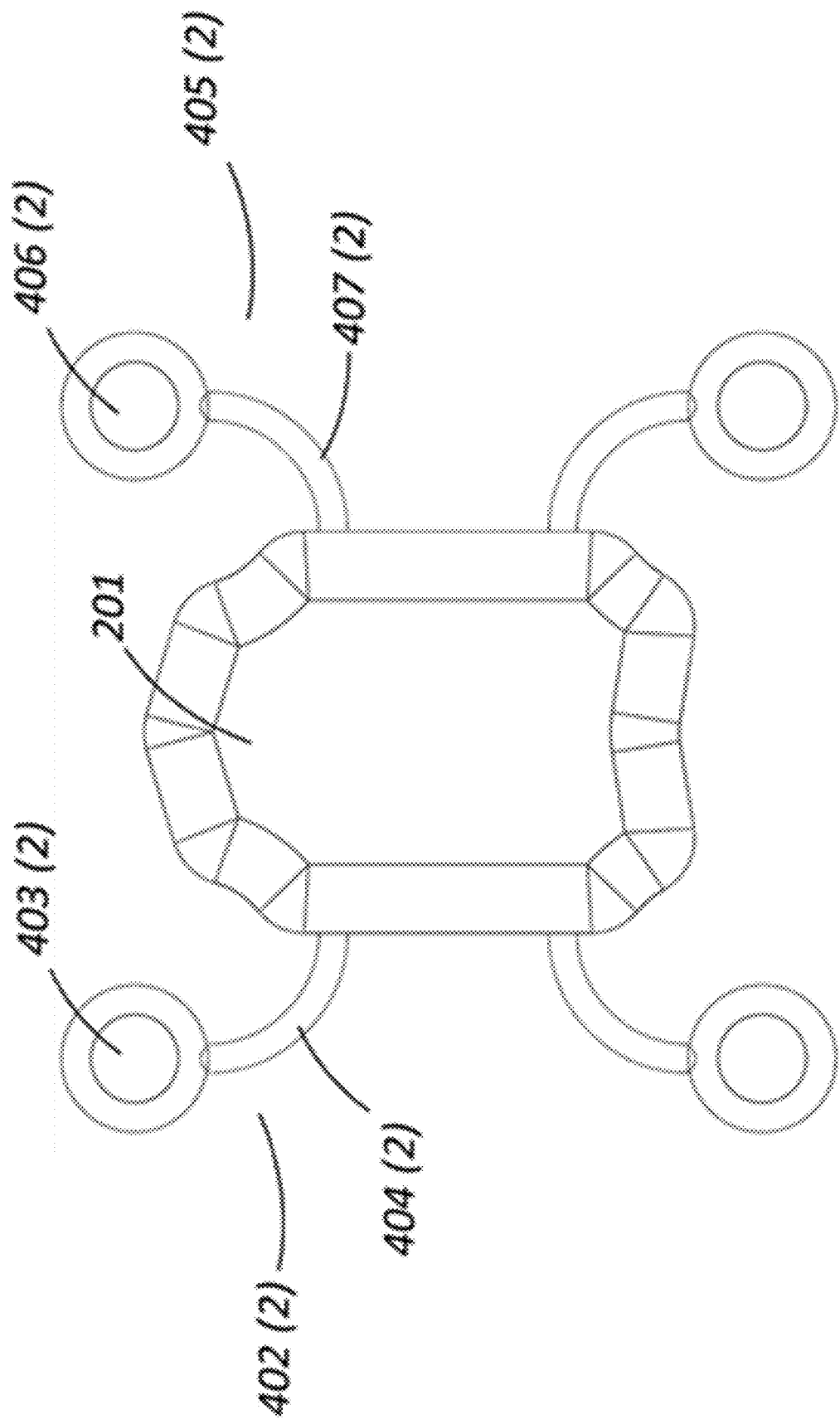
FIG. 4 illustrates an apparatus with four circular radius legs, in accordance with one or more embodiments.
Figure 5:
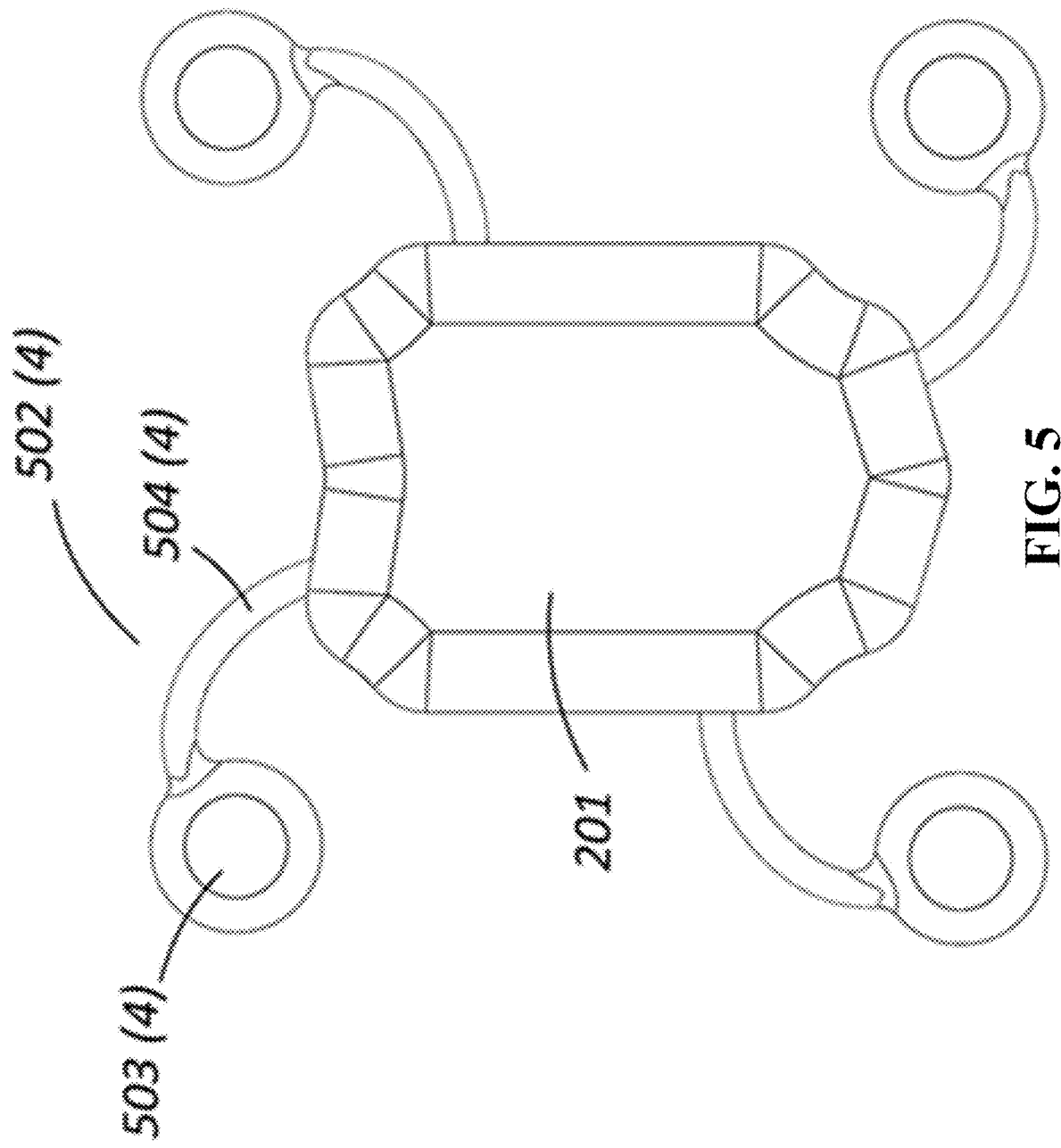
FIG. 5 illustrates an apparatus with four legs positioned with curvature in the same direction, in accordance with one or more embodiments.

In yet another embodiment, as illustrated in FIG. 4, the curvature of legs 404 and 407 protruding from device housing 201 is circular (e.g., with a radius of >10 mm). The length of flexible portion 404 and 407 can be modified to affect ECG vector length as well as to change the spring constant of legs 402, 405. In this embodiment legs 402 and 405 protrude from the left and right sides of device housing 201, but can be modified to protrude from other positions, for example as shown in FIG. 5. This embodiment can use any cross-sectional area for flexible portion 404, 407 of the legs 402, 405 as described previously.

In yet another embodiment, illustrated in FIG. 5, legs 504 protrude from housing 201 and represent either a quadratic spline pattern or a circular radius, with all oriented in the same direction, either clockwise or counterclockwise. This embodiment of the legs 502 may be beneficial as it allows the device housing 201 to rotate uniformly with movements of the body, acting as a strain relief for the electrodes, increasing signal quality and patient comfort. This embodiment can be modified so legs 502 are attached to different locations of housing 201, or that the feet 503 are positioned any distance from the housing 201. However, design principles remain the same. This embodiment can also utilize any cross sectional design for flexible portion 504 of the legs 502, as described earlier.

Figure 6:
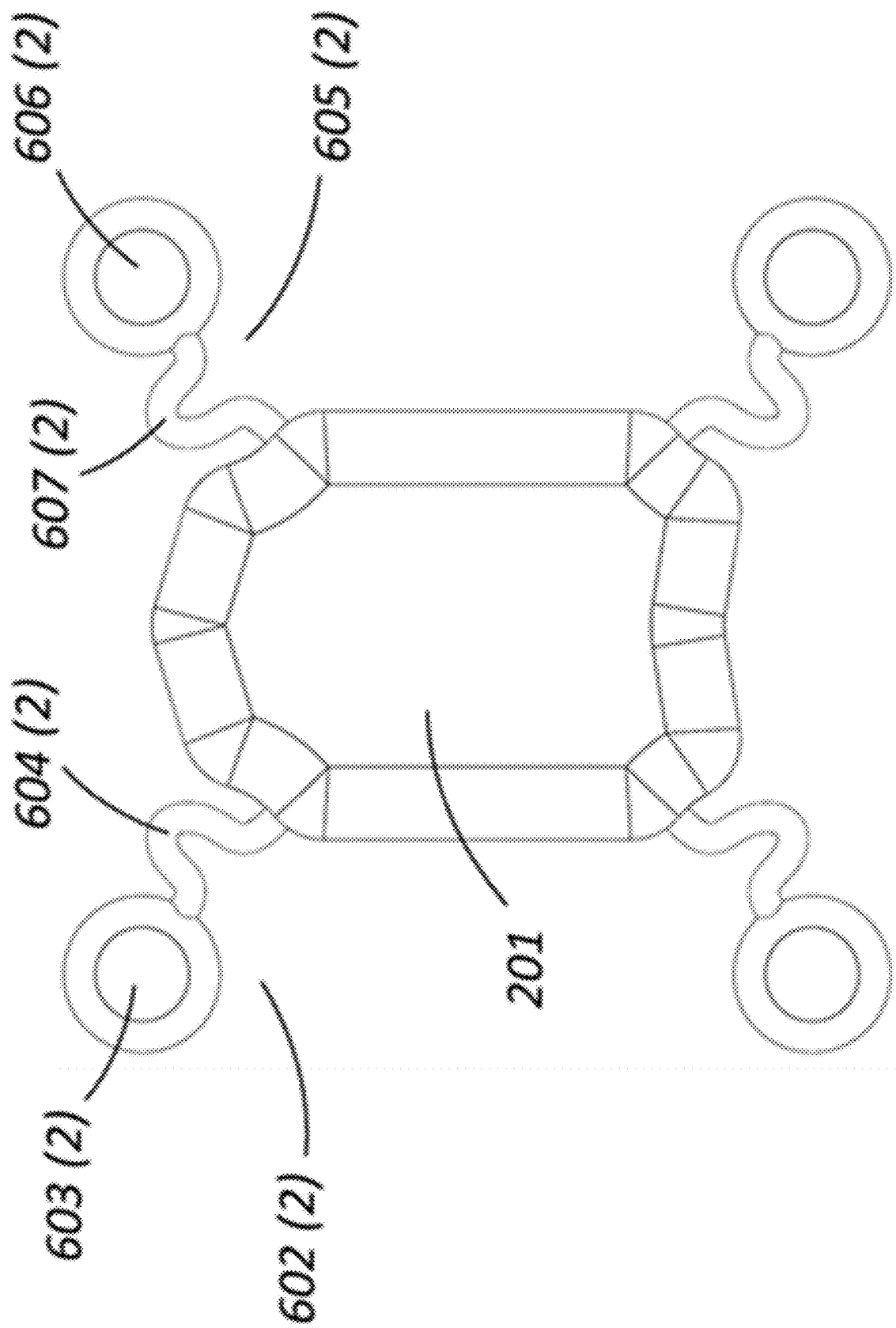
FIG. 6 illustrates an apparatus with four S-shaped legs, in accordance with one or more embodiments.

In yet another embodiment, as illustrated in FIG. 6, the device contains a housing 201 with "S" shaped legs 602 and 605 protruding from it with four feet 603 and 606 at the ends which attach to ECG electrodes. The cross-sectional design of the legs 604, 607 can vary as described earlier. The illustration shows four legs, but this embodiment can also be used with at least two or more legs 602 and 605 which connect to ECG electrodes on the skin. In some embodiments, it may be useful for legs 602 and 605 to have identical designs.

Figure 7:
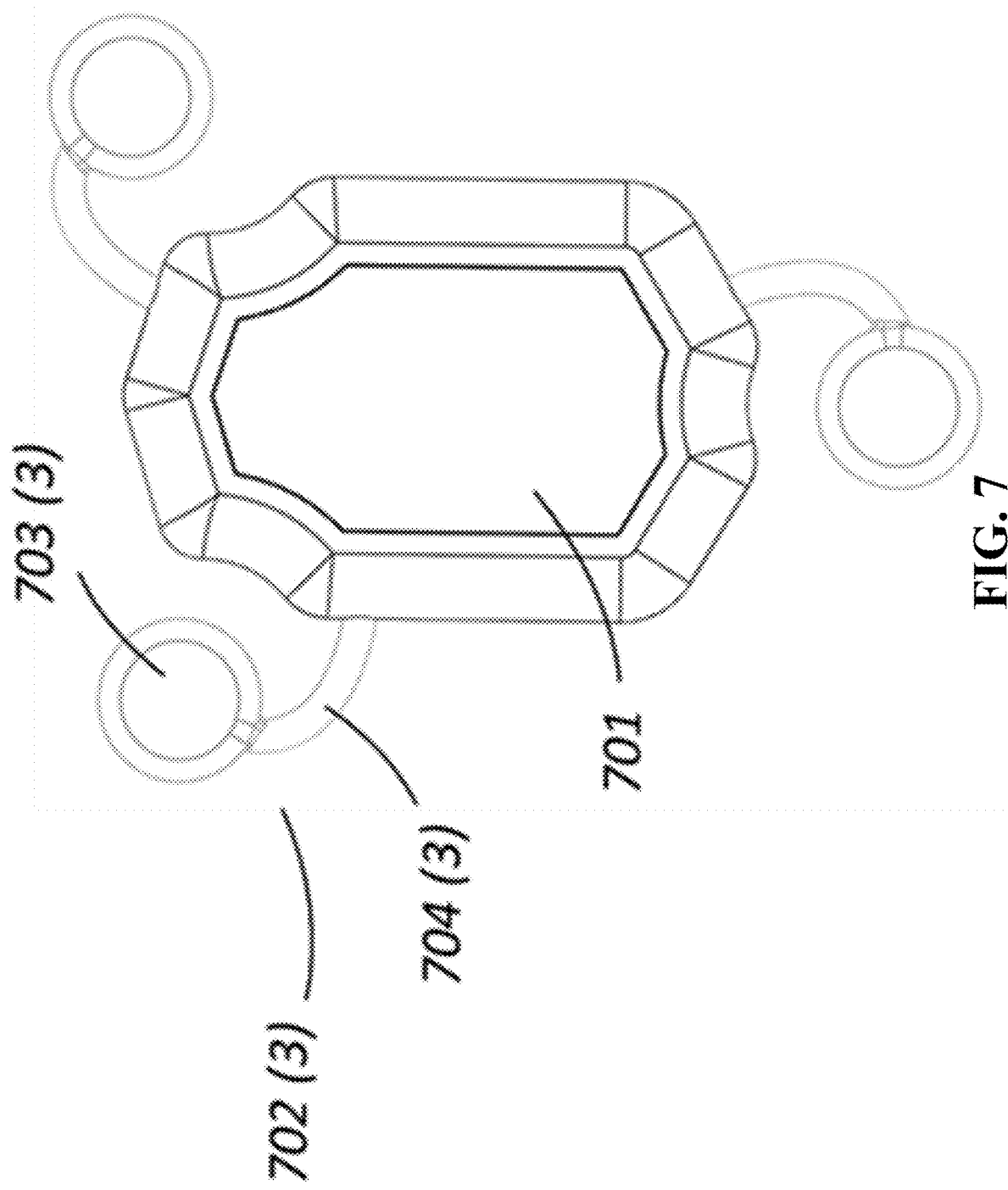
FIG. 7 illustrates an apparatus with three legs, in accordance with one or more embodiments.

In yet another embodiment, as illustrated in FIG. 7, there are 3 legs 702, in any of the shapes, patterns, and cross sections mentioned herein, protruding from housing 701. This embodiment can be utilized so that either two or all three legs 702 provide an electrical connection from ECG electrode to an amplifier contained within the housing.

Figure 8A:
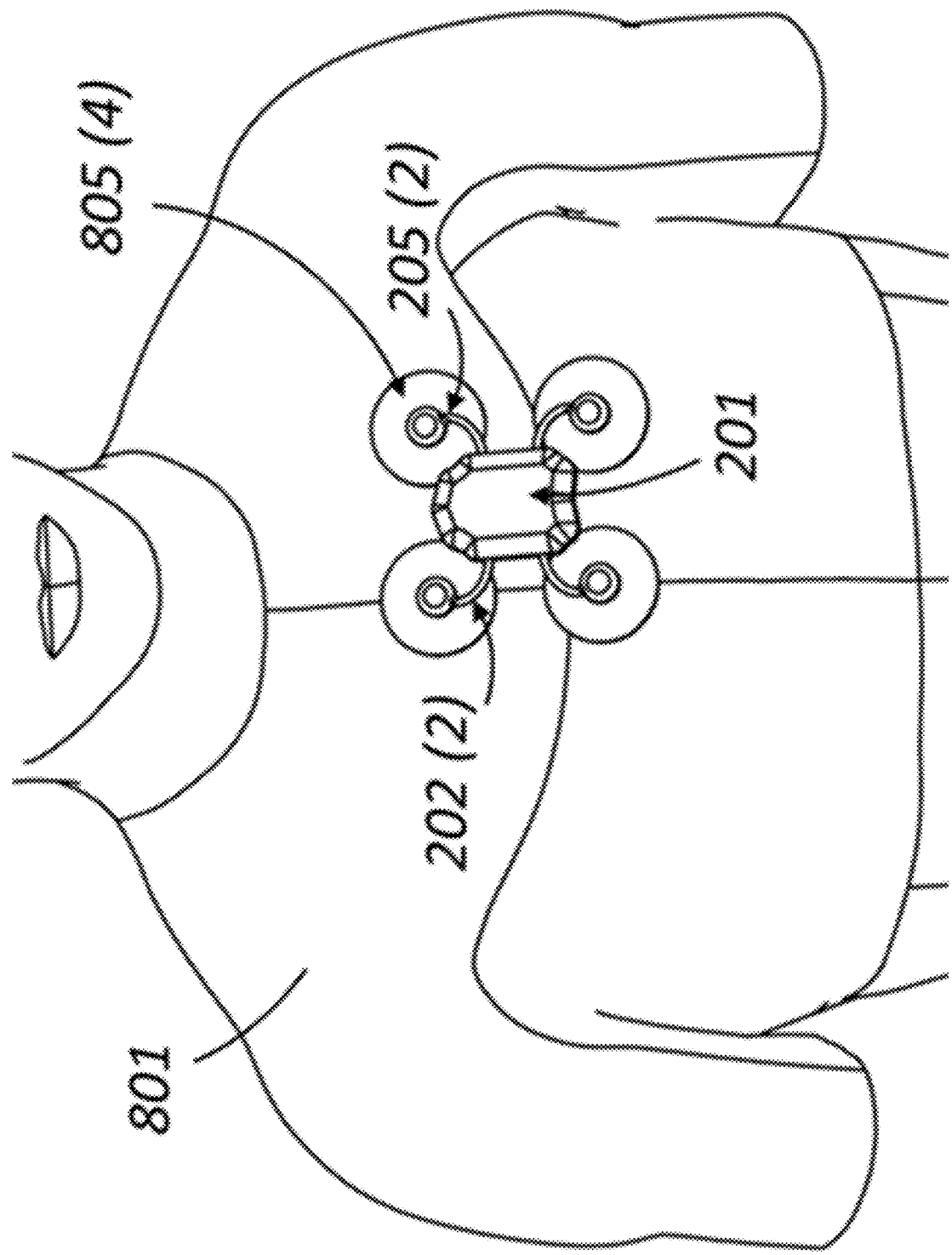
FIGS. 8a and 8b illustrate a device worn on human torso respectively in alternate locations, with an ECG electrode attached to each leg, in accordance with one or more embodiments.
Figure 8B:
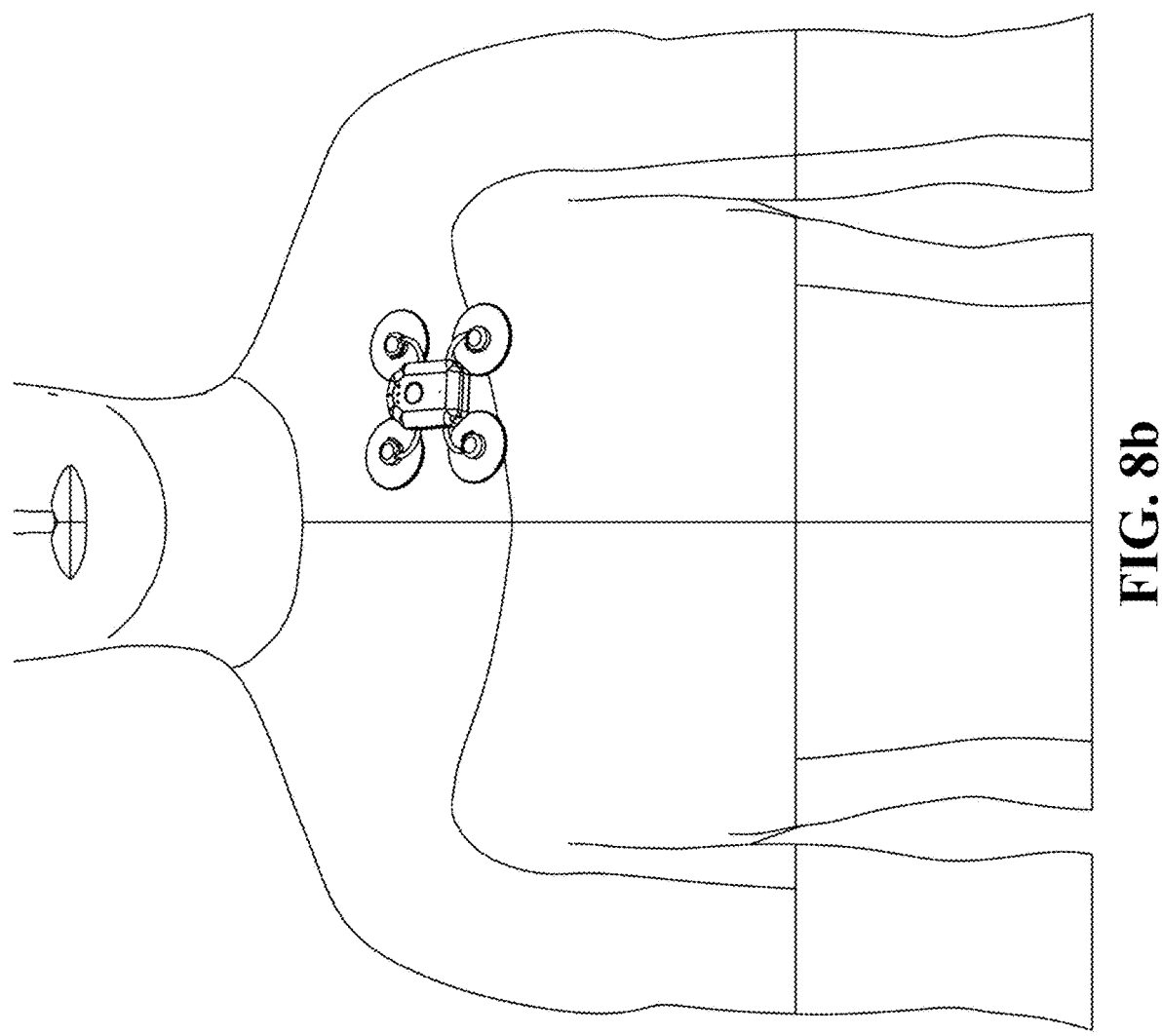

In yet another embodiment, illustrated in FIG. 8a, device 201 is worn on a human torso 801 using four standard ECG electrodes 805. Each ECG electrode 805 is attached to a leg 202, 205. It is positioned so that the device housing 201 is positioned with the longest dimension in the vertical direction. In some patients it may be beneficial to place two of the four ECG electrodes 805 on the sternum with the other two positioned on the left side of the chest. The skin on the sternum does not move much during body movements, and it is a good vector position to detect P waves. Different positioning of the electrodes 805 may also be used as they may be found to improve either signal quality or comfort for the user. For example, it may be more comfortable for some patients to wear the device in the location shown in FIG. 8b. In addition, if worn for an extended period of time, when changing electrodes the user may move the position slightly in order to place electrodes 805 on different skin. This is beneficial as it has been found that electrodes may have adverse effects on skin for many users when worn in the same location for long periods of time.

Figure 9:
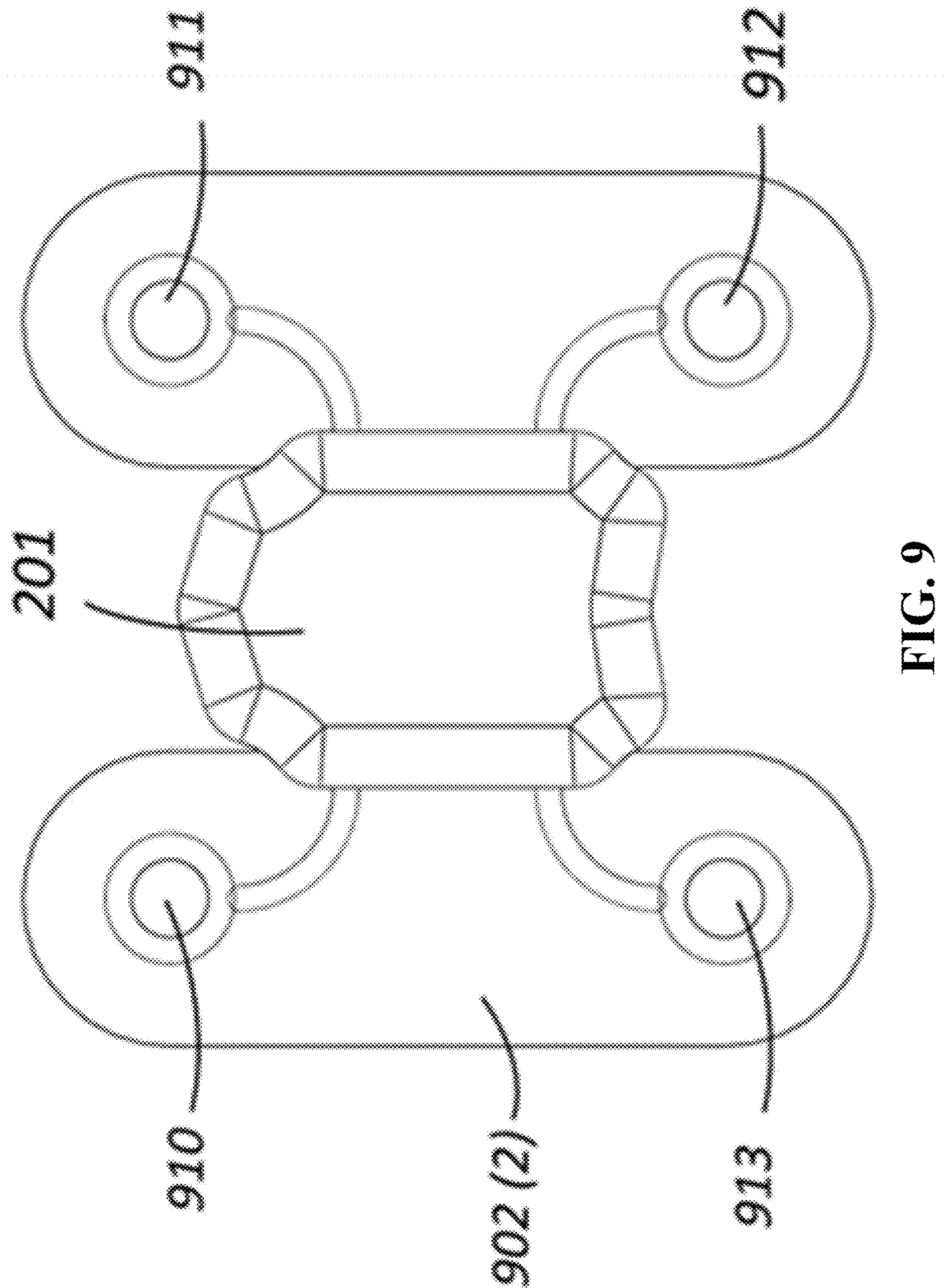
FIG. 9 shows an apparatus with four legs, with two electrodes embedded with two adhesive patches, in accordance with one or more embodiments.

In yet another embodiment, as illustrated in FIG. 9, device 201 is attached to two ECG electrode patches 902, with each electrode patch having two electrodes in contact with the patient's skin. In one embodiment, legs 910 and 913 attach to one of patch 902, and legs 911 and 912 attach to a second patch 902. In another embodiment, electrodes 902 are rotated 90° so legs 910 and 911 attach to one electrode patch 902 and legs 912 and 913 attach to the other electrode patch 902. Use of a patch containing two electrodes can be integrated with all embodiments of leg design/quantities discussed herein.

In one embodiment, device 201 includes three LED indicators to communicate the operating status of the device. These include one or more of:

A State indicator to indicate the operating state of the device

A battery indicator to indicate the charge status of the battery

A cell indicator to indicate the status of the cellular connection.

Figure 10:
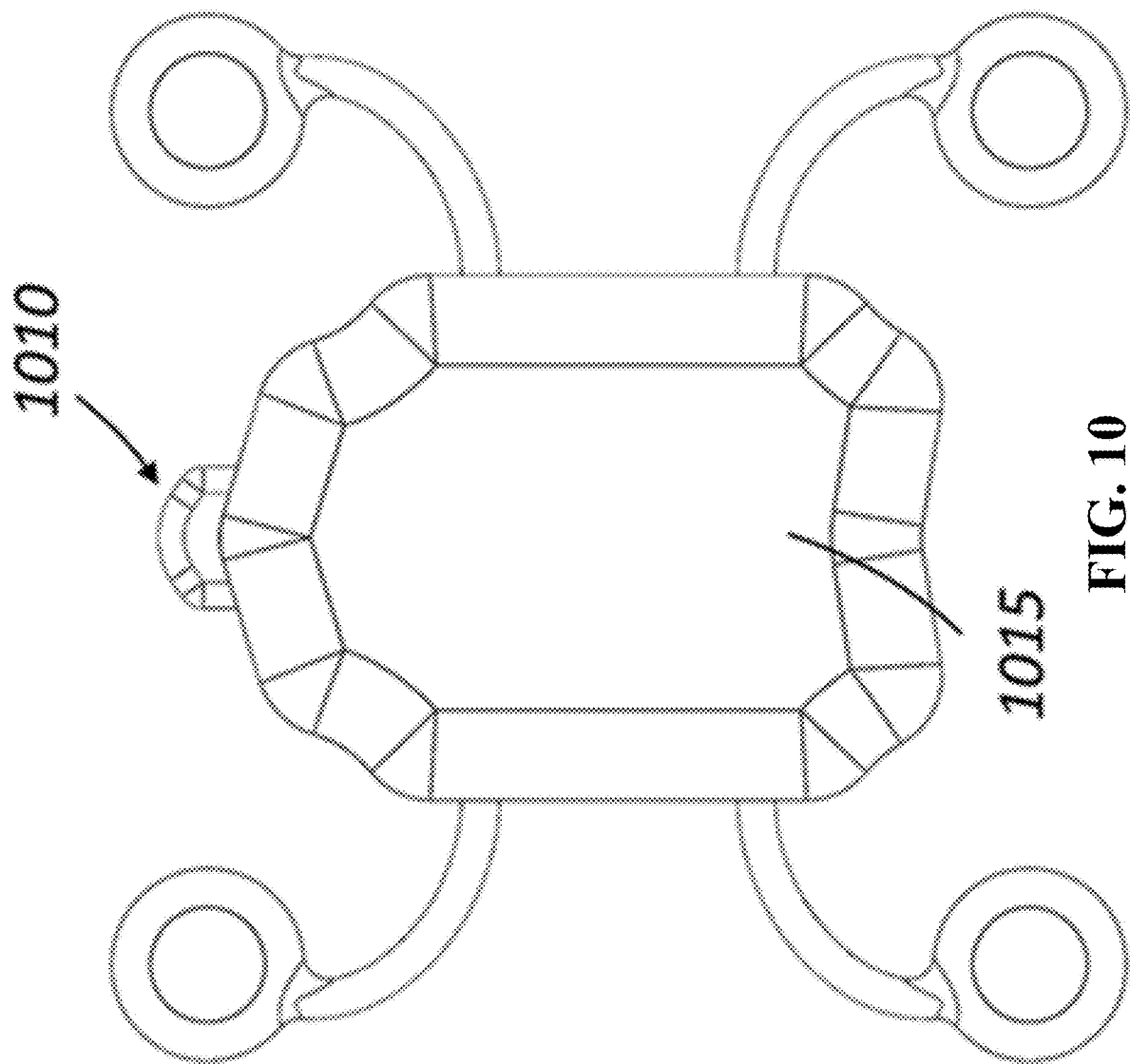
FIG. 10 shows an apparatus with hook to attach to a lanyard, in accordance with one or more embodiments.

In another embodiment, as illustrated in FIG. 10, housing 1015 includes a loop 1010 which can be used to attach the device to a lanyard worn around the neck. This feature when connected to a lanyard may be useful if the device were to come loose from the skin, as the lanyard would prevent the device from falling completely off the patient and becoming lost or damaged. This loop may be located anywhere on housing 1015 and may be used with a variety of lanyard styles.

Figure 11:
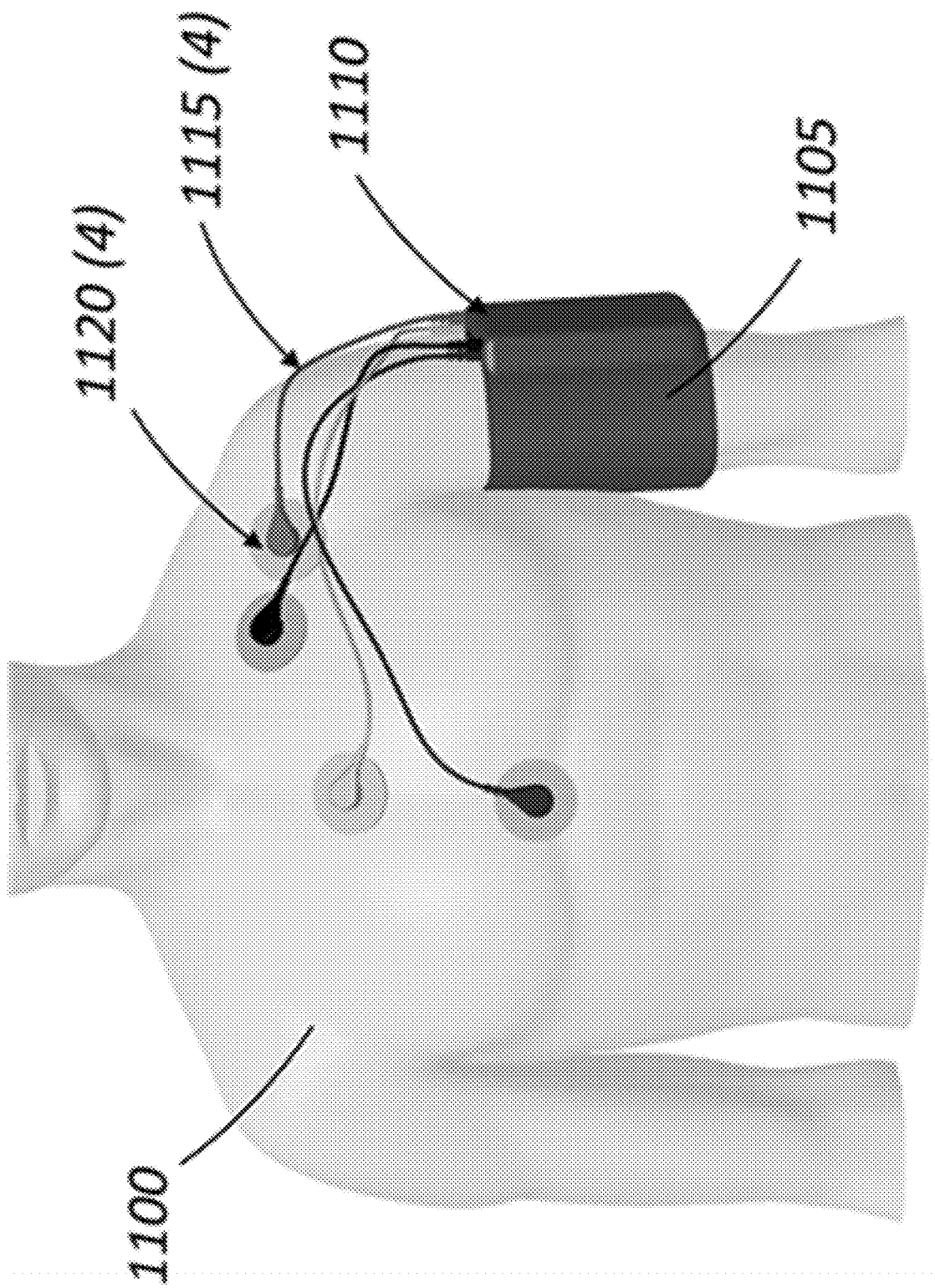
FIG. 11 shows a patient wearing a device with lead wires on arm band, in accordance with one or more embodiments.

In another embodiment, as illustrated in FIG. 11, the device 1110 is worn within an arm band 1105 and the ECG electrodes 1120 are attached to the body 1100 and electrically connected to the device via lead wires 1115. Wearing the device 1110 in this manner may be beneficial for patient comfort and signal quality. Potential benefits include an improvement in signal quality due to a reduction in movement of the lead wires 1115 and increased patient comfort, especially in patients who live very active lifestyles. To allow the arm band to accommodate a range of upper arm sizes, it may be beneficial to fabricate the arm band of an elastic material with a hook-and-loop type fastener (e.g., nylon or other material) into the arm band to provide for adjustment of the inner diameter. In addition, it may be beneficial to incorporate a mesh material over the device to render the front surface visible for the purpose of viewing the screen and identifying the location of buttons on the keypad.

Figure 12:
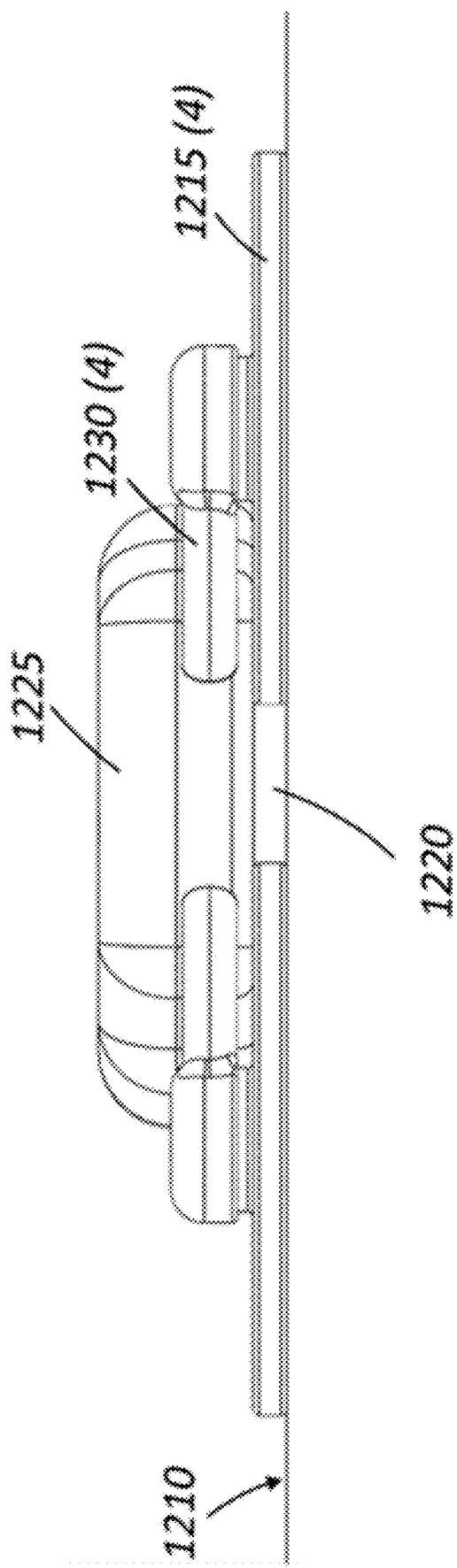
FIG. 12 illustrates a device attached to electrodes showing how the design accommodates airflow between skin surface and housing, in accordance with one or more embodiments.

In another embodiment, referencing FIG. 12, legs 1230 protrude from the device housing 1225 and are positioned in such a way that the device housing is located above the surface 1210 of the body. The housing and legs are designed such that a gap 1220 is present between body surface 1210 and device housing 1225. This gap may be beneficial to user comfort as it will allow air to flow between the skin and device.

In another embodiment, the legs 1230 protruding from the device housing 1225 are positioned in such a way that the device housing rests upon the electrodes 1215 and provides a slight force towards the body 1210. This force may be beneficial in helping the device to maintain its position on the body 1210.

Figure 13:
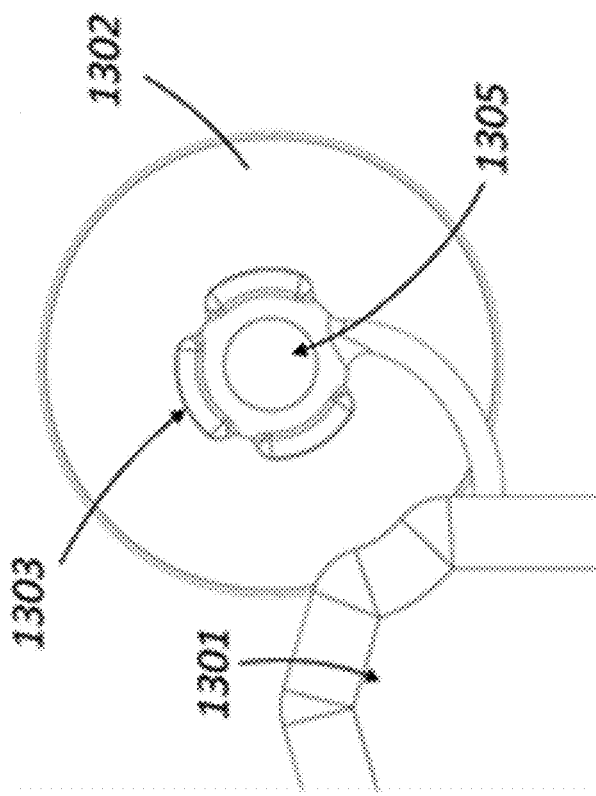
FIG. 13 illustrates feet with a feature to facilitate detachment from electrodes, in accordance with one or more embodiments.
Figure 13:
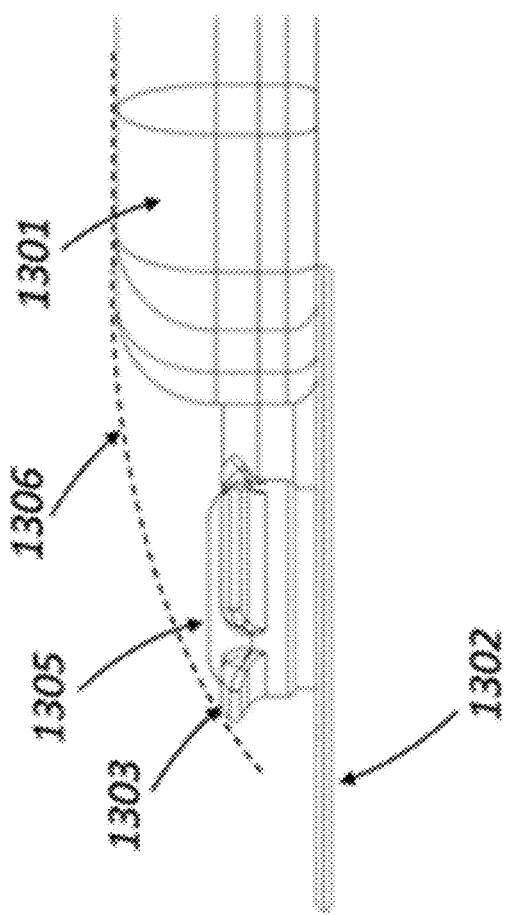

In another embodiment, referencing FIG. 13, a release feature 1303 is included on each foot 1305. The release feature 1303 may be useful to make it easier to disconnect feet 1303 from electrode 1302. In one embodiment, the profile of the feature 1303 and device 1301 are designed such that a curvature 1306 is followed. This curvature 1306 may be useful to mitigate the risk of items catching on the feature 1303 and accidentally disconnecting a foot 1305 from electrode 1302. In alternate embodiments, this feature 1303 may be limited to a portion of the circumference of foot 1305.

Figure 14:
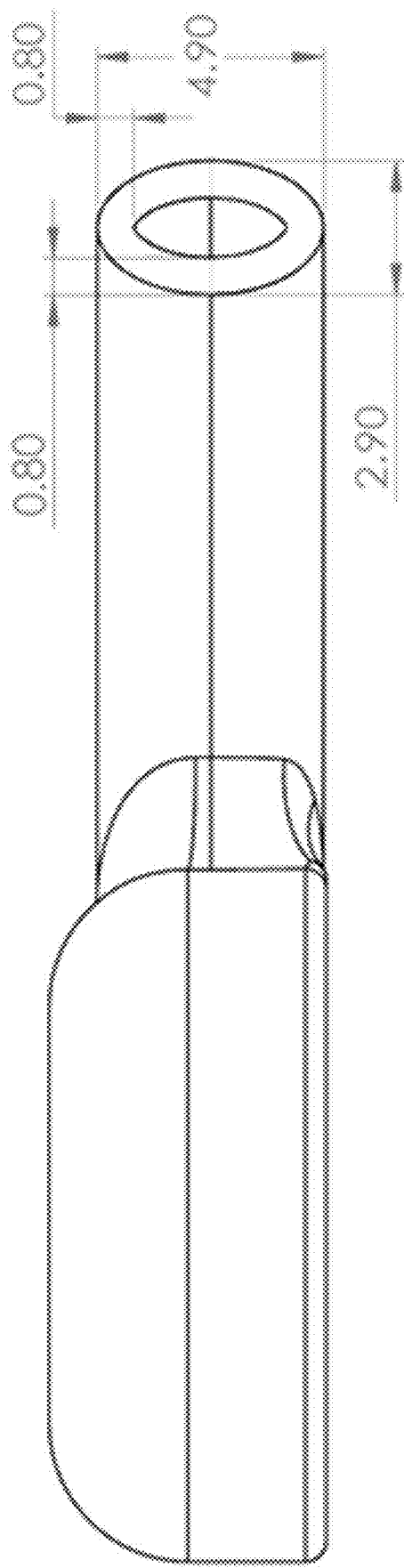
FIG. 14 illustrates a leg cross section of an apparatus, in accordance with one or more embodiments.

Referring to FIG. 14, the dimensions of an embodiment for the cross section of the legs are shown. This embodiment was 3D printed is 2 different materials, each with different mechanical properties. One material was CarbonResin EPU 40 from Carbon (Redwood City, CA) printed using their Continuous Liquid Interface Production (CLIP) 3D printing technology. The other material was TPU 70 produced with Selective laser sintering (SLS) technology. Both material prints had the same design with an oval cross-section that is 4.9×2.9 mm and material thickness being 0.80 mm on all sides. The hardness of material TPU 70 is Shore A 70 and the hardness of material EPU 40 is Shore A 68. This drawing shows a cavity in the center of the leg to accommodate 3D printing. More often, the core of the leg will be occupied by a wire connecting snap 208 with AFE 102. In some embodiments a material having a spring property may also be present in the core to modify the spring properties of the leg.

Measurements of spring constant were obtained on legs fabricated of the two materials discussed herein. Both materials and cross section exhibited properties that provided good performance of legs 202 and 205 in that the legs were able to accommodate changes in posture and movement when placed on the chest. The mechanical properties of the legs shown in the table below represent one design, but it should be recognized that the mechanical properties of other materials and design may differ from those in the table and still provide adequate performance. X-Y spring constant is the spring constant in the plane parallel to the body of the device. Z spring constant is the spring constant for movement perpendicular to the plane of the device.

TABLE 2

Example measurement of spring constant for two materials with leg of cross section shown in FIG. 14.

| Leg cross section design | Material | XY Plane average spring constant, k | Z Plane average spring constant, k |
| --- | --- | --- | --- |
| v1 | TPU 70 | 11.90 N/m | 16.91 N/m |
| v1 | EPU 40 | 5.69 N/m | 10.27 N/m |

Figure 15:
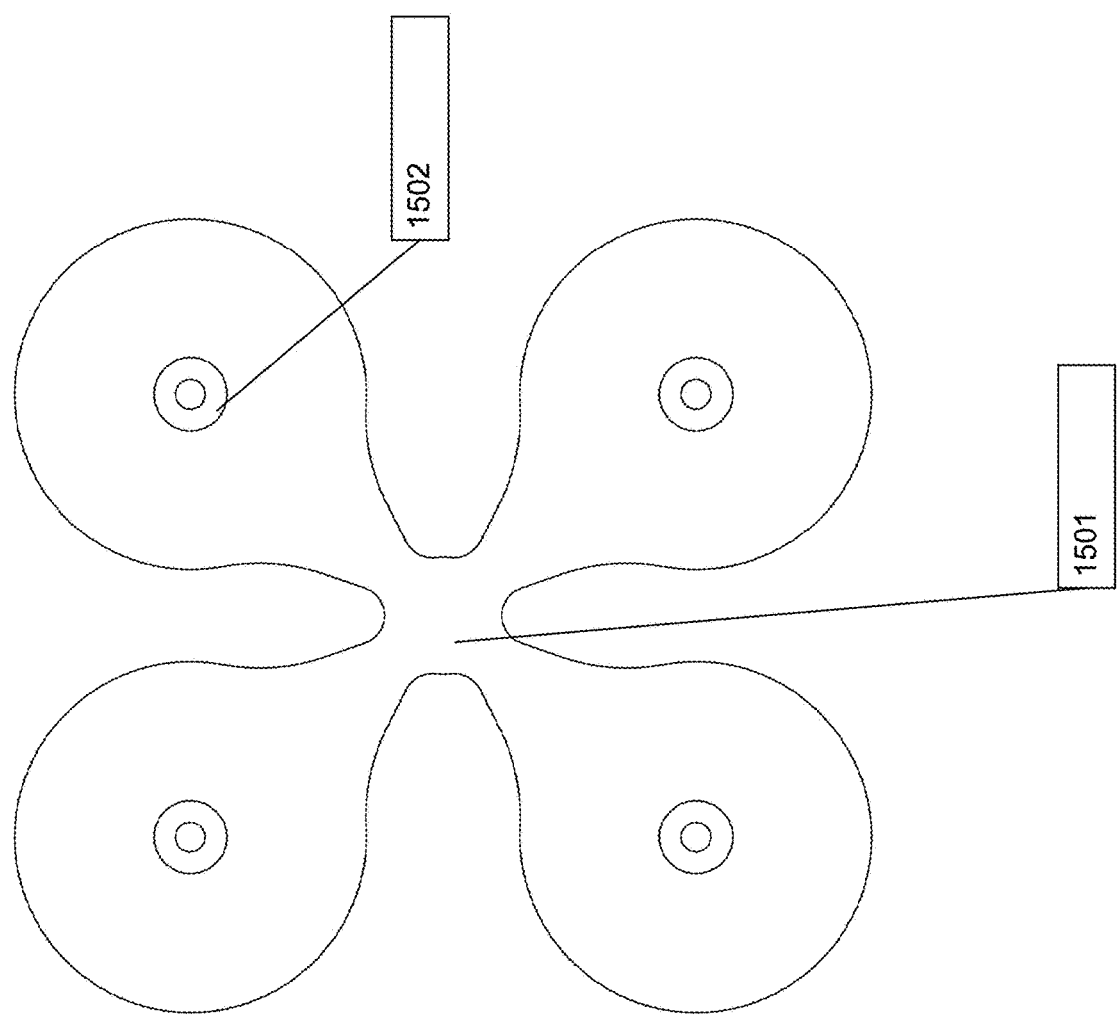
FIG. 15 shows a patch including four sensing electrodes, in accordance with one or more embodiments.

In one embodiment, referring to FIGS. 2 and 15, device 201 is attached to skin patch 1501 containing four ECG sensing electrodes. Snaps 1502 may be placed at a distance matching the positioning of feet 203 and 206. In some embodiments, this arrangement may have the benefit of providing an easier way for the patient to apply all four electrodes to the skin and then attach device 201 to the electrodes on the skin once the electrodes are in position.

In an alternate embodiment, a template is provided with openings corresponding the locations of the snap in electrodes 805. The template can be positioned on the skin at the location where the device is to be attached and a marker (e.g. ink or colored dot) can be used to note the location of the center of electrodes 805. Electrodes 805 can hence be attached to the skin at locations corresponding to the locations of feet 203 and 206.

Figure 16:
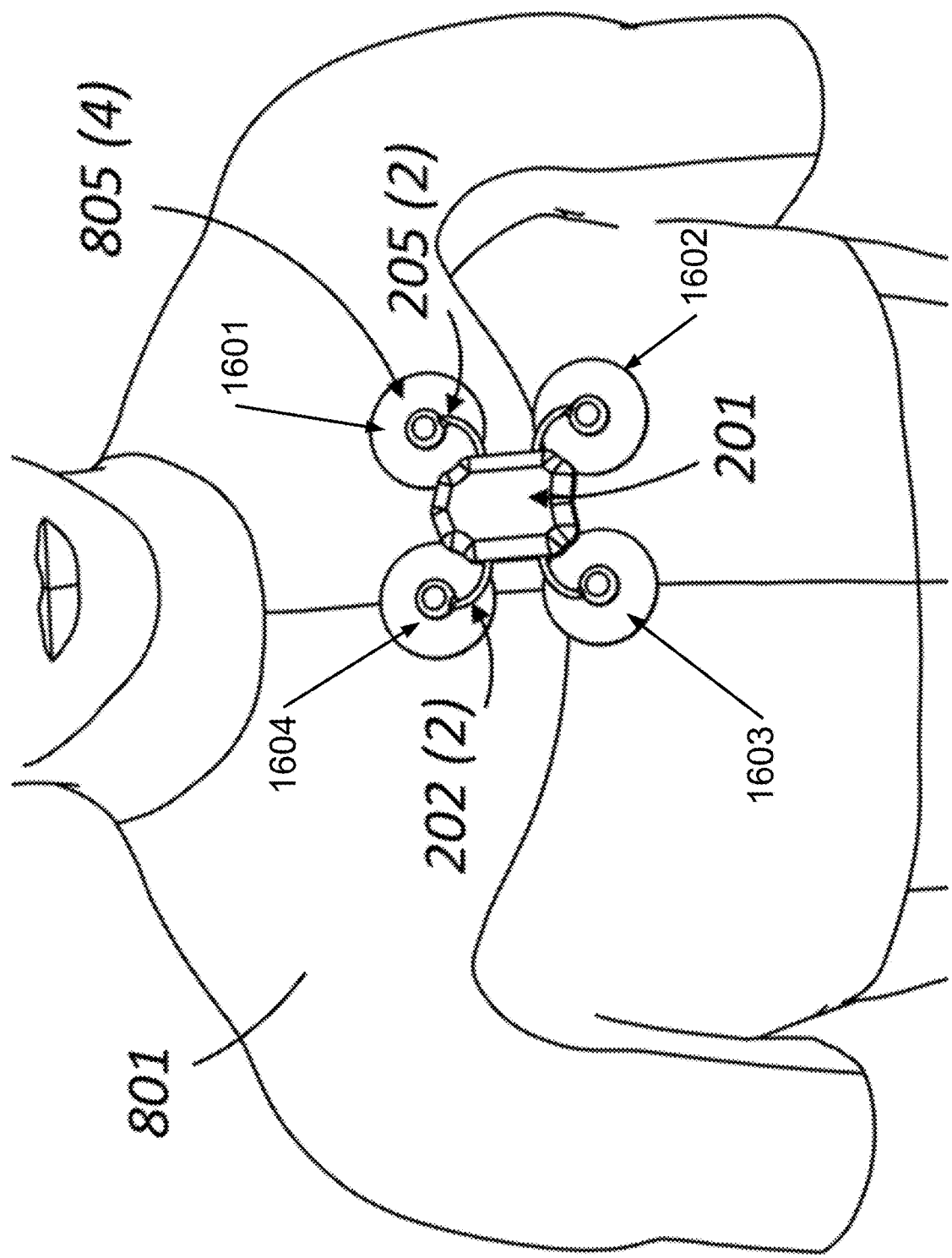
FIG. 16 illustrates lead reassignment to measure alternate ECG vectors, in accordance with one or more embodiments.

In some embodiments, referring to FIGS. 1, 2, and 16, the patient may not place device 201 on the chest in the correct orientation, resulting in a potential inconsistency in ECG morphology. In one embodiment, referring to FIG. 16, electrode 1603 is assigned to the right leg (RL) input of analog front end circuitry 102, 1602 is assigned to left leg (LL) input, 1601 is assigned to left arm (LA) input, and 1604 is assigned to right arm (RA) input. When configured in the manner, the two ECG signals (vectors) (RA-LL and RA-LA) measured by device 201 have a recognized morphology. However, if the patient removes the device to change electrodes and replaces the device at a 90-degree clockwise angle relative to that shown in FIG. 16, the morphology will be significantly different than prior to the electrode change. In one embodiment, (in part enabled because of the symmetry of the device) the morphology can be restored to a morphology similar to the previous morphology by reassigning the leads so that 1603 is now RA, 1601 is now LL, 1602 is now RL, and 1604 is now LA. In one embodiment, lead reassignment is accomplished by sending a device configuration file from the server to device 201 with definitions for how the analog front end should be reconfigured. In one embodiment, the analog front end is a Texas Instruments (Dallas, TX) ADS1293. This chip contains internal switches to reassign the inputs based upon the content of registers contained within the chip.

Figure 17:
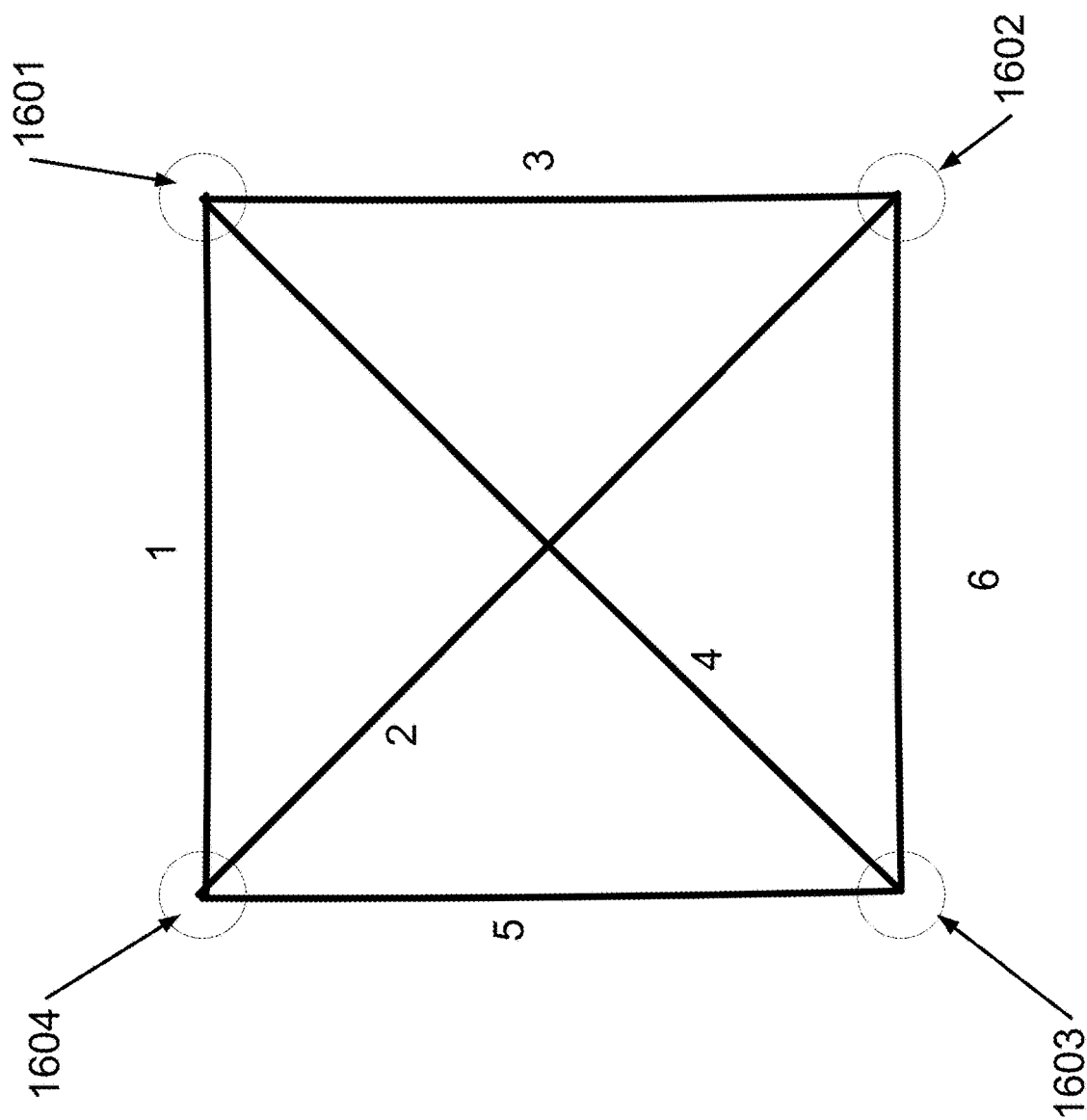
FIG. 17 showing ECG vectors that can be measured by reconfiguring ECG lead assignments in the analog front end, in accordance with one or more embodiments.

In some embodiments, referring to FIGS. 16 and 17, the placement of device 201 on the skin may not provide for the optimal vector orientation to maximize QRS and ventricular ectopic beat (VEB) detection. In this case, it can be useful to reassign the leads to compute ECG vectors that provide signal that enable improved QRS and VEB detection. By reassigning the leads, the vector orientation may be improved. In one embodiment, the six vectors (1, 2, 3, 4, 5, 6) shown in FIG. 17 are computed, such as by measuring ECG vectors by reconfiguring ECG lead assignments in the analog front end three vectors (1, 2, and 3 in FIG. 17) derived from a first lead configuration and three from a second lead configuration. If RL is assigned to electrode 1603, RA to 1604, LA to 1601, and LL to 1602, then two of the three associated vectors are computed as electrode 1604—electrode 1602 (RA-LL), and electrode 1604—electrode 1601 (RA-LA). The third vector associated with this lead configuration is computed using vector algebra as electrode 1601—electrode 1602 using the vectors RA-LL and RA-LA.

To obtain two additional vectors (5 and 4 in FIG. 17), RL is assigned to electrode 1602 and RA is assigned to electrode 1603, LL is assigned to 1604, and LA is assigned to 1601. The $6^{th}$ vector (6 in FIG. 17) can be obtained by assigning LA to 1602, LL is assigned to 1604, RA is assigned to 1603, and RL is assigned to 1601. Vector 6 is then RA-LA. In some embodiments four lead vectors are calculated to match lead reassignment to device orientation.

Once all 6 vectors are computed, eigenvectors are computed using eigenvalue decomposition. In another embodiment, principal component analysis (PCA) is used to compute principal components. Principal components (or basis vectors) represent the degree of contribution from each of the six vectors to the orthogonal basis spanned by optimal vectors. In one embodiment, the PCA coefficients are evaluated to select the two best vectors out of the six computed vectors. Similarly, in another embodiment, eigenvectors are evaluated to find vectors that most closely approximant an optimal orthogonal basis.

In one embodiment, the battery life of the device is extended by reducing the frequency of communications in an adaptive manner based upon state of charge of the battery or other information about the operating status of the device. In one embodiment, the typical time between scheduled connections to the server is 15 minutes. In the absence of detection of an arrhythmia or symptomatic event requiring immediate communication to the server, the device may switch to a less frequent communication interval to save power. For example, in one embodiment, if it is recognized that the patient is sleeping based upon heart rate measurements, the device may change the server connection interval from 15 minutes to 2 hours to save power. In another embodiment, when the battery state of charge is less than 30%, the device may change the server connection interval from 15 minutes to 2 hours to save power.

Various blocks, modules or other circuits may be implemented to carry out one or more of the operations and activities described herein and/or shown in the figures. In these contexts, a "block" (also sometimes "logic circuitry" or "module") is a circuit that carries out one or more of these or related operations/activities (e.g., obtaining a signal, digitizing a signal, computing aspects indicative of a physiological characteristic). For example, in certain of the above-discussed embodiments, one or more modules are discrete logic circuits or programmable logic circuits configured and arranged for implementing these operations/activities, as in the circuit modules shown in FIG. 1. In certain embodiments, such a programmable circuit is one or more computer circuits programmed to execute a set (or sets) of instructions (and/or configuration data). The instructions (and/or configuration data) can be in the form of firmware or software stored in and accessible from a memory (circuit). As an example, modules may include a combination of a CPU hardware-based circuit and a set of instructions in the form of firmware, where one module includes a CPU hardware circuit with one set of instructions and another module includes a the same or a different CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform operations/activities as characterized herein.

Based upon the above discussion and illustrations, various modifications and changes may be made to embodiments and implementations characterized herein, without strictly following such exemplary embodiments and applications. For example, wearable electrodes as depicted may be implemented in different arrangements or situations, as noted herein. In addition, the various embodiments described herein may be combined in certain embodiments, and various aspects of individual embodiments may be implemented as separate embodiments. Such modifications do not depart from the true spirit and scope of various aspects of the invention, including aspects set forth in the claims.

The invention claimed is:

1. An apparatus for monitoring heart rhythm of a patient, the apparatus comprising:
   a housing having a perimeter;
   within the housing, amplifying circuitry and digitizing circuitry configured to amplify and digitize ECG signals;
   three or more legs extending from the perimeter of the housing, each configured to provide an electrical connection from an ECG skin electrode to the amplifying circuitry and to obtain the ECG signals from the ECG skin electrodes;
   computing circuitry for processing the digitized ECG signals;
   communication circuitry configured for communicating data corresponding to the ECG signals;
   data storage circuitry configured to store data corresponding to the ECG signals; and
   a charge storage circuit configured to provide power to the circuitry, computing circuitry, and communication circuitry, wherein the legs are configured to:
      mechanically connect to skin electrodes and to support the weight of the housing and its contents in response to the skin electrodes being adhesively secured to skin with the legs and housing suspended away from a surface of the skin, and
      facilitate movement of each of the skin electrodes to which the legs are connected relative to a portion of the housing to which the leg is connected and relative to the other skin electrodes.

2. The apparatus of claim 1, wherein the communication circuitry includes cellular modem circuitry inside the housing.

3. The apparatus of claim 2, wherein the computing circuitry is configured and arranged to reduce power consumption for effecting communications via the cellular modem circuitry while worn by the patient, by denoising the ECG signals and effecting data compression.

4. The apparatus of claim 3, wherein the computing circuitry is configured and arranged to denoise the ECG signals and effect data compression thereof to reduce the volume of data such that radiated radio frequency energy required for communication of the data is below 1.6 W/kg, averaged over 1 gram of the patient's skin to which said housing is in direct contact with.

5. The apparatus of claim 2, wherein the power required for monitoring the heart rhythm of a patient is sufficiently low that the amplifying circuitry, digitizing circuitry, computing circuitry, cellular communication circuitry, data storage circuitry, and charge storage circuitry can be packaged within a housing having a volume of less than 33 cc.

6. The apparatus of claim 5, wherein the charge storage circuit includes a battery having a life greater than 3 days when powered for obtaining and processing the ECG signals, and for communicating the data corresponding to the ECG signals.

7. The apparatus of claim 1, wherein the legs are configured and arranged with a stiffness and flexibility that, with a weight of the apparatus, limits torque applied to the adhesively secured skin electrodes to below a threshold amount of torque that would counter the adhesive and lift one of the electrodes off the patient's skin.

8. The apparatus of claim 7, wherein the legs are configured and arranged with a stiffness and flexibility that, with a weight of the apparatus, facilitate movement of the housing relative to the patient's skin.

9. The apparatus of claim 1, wherein the legs are fabricated of a material that renders them flexible wherein each leg is connected to a lateral surface of the housing and is configured to facilitate movement of a skin electrode to which it is connected toward and away from each of the other skin electrodes, while the skin electrodes are adhered to a patient.

10. The apparatus of claim 9, wherein the material is selected from the group of: Thermoplastic Elastomers (TPE), Thermoplastic Vulcanizates (TPV), Thermoplastic Urethane (TPU), Flexible Polyvinyl Chloride (PVC), silicone rubber, and a combination thereof.

11. The apparatus of claim 1, further including the skin electrodes, the skin electrodes including a single sensing surface configured to contact the skin for obtaining the ECG signals.

12. The apparatus of claim 1, further including the skin electrodes, the skin electrodes including four electrodes in two arrays, each array including two sensing surfaces.

13. The apparatus of claim 1, further including the skin electrodes, the skin electrodes configured in an array, configured and arranged to connect each electrode to a leg.

14. The apparatus of claim 1, wherein the legs are flexible in to facilitate movement of the skin electrodes in an X-Y plane along which the legs extend from the housing.

15. The apparatus of claim 1, wherein the legs are flexible in a Z axis extending toward the patient, when the legs are secured to the skin electrodes adhered to the skin, to allow movement of the housing along the Z axis.

16. The apparatus of claim 1, wherein the legs are curved.

17. The apparatus of claim 1, wherein the legs are S-shaped.

18. The apparatus of claim 1, wherein the communication circuitry includes a wireless communications circuit.

19. The apparatus of claim 1, wherein the communication circuitry includes a wired communications circuit.

20. The apparatus of claim 1, wherein the legs include an insert with a spring constant between 5 N/m and 20 N/m in the X-Y plane and between 10 N/m and 25 N/m along the Z axis.

21. The apparatus of claim 1, wherein the three-two or more legs are configured and arranged with the housing and the electrodes to reduce electrode motion noise by mechanically absorbing shock relative to the electrodes.

22. The apparatus of claim 1, further including the skin electrodes, the skin electrodes including three electrodes, each electrode being configured to move relative to one another and relative to the housing.

23. An apparatus comprising:
electrodes configured to attach to the skin of a patient and to obtain ECG signals from the patient;
a housing including:
circuitry configured to digitize and remove noise from ECG signals obtained from the electrodes and to transmit signals corresponding to the ECG signals, and
a power source configured to power the circuitry; and
legs connected to a perimeter of the housing, connecting the housing to the electrodes and being configured and arranged with the housing and electrodes to:
suspend the housing relative to the skin to which the electrodes are attached, and
with the housing suspended, maintaining the electrodes in contact with the skin and obtaining the ECG signals via the electrodes.

24. The apparatus of claim 23, wherein the legs exhibit a stiffness that is configured to allow movement of the electrodes relative to each other while maintaining electrical contact between the electrodes and the skin that is sufficient for obtaining the ECG signals.

25. The apparatus of claim 23, wherein the legs are configured and arranged with the electrodes to suspend the housing relative to the skin with the housing adjacent to and in contact with the patient's chest, while allowing movement of the housing relative to the patient's chest.

26. The apparatus of claim 23, wherein:
the housing weighs less than 47 grams;
the digitizing circuitry includes a data storage circuit to store data corresponding to the ECG signals; and
the power source includes charge storage circuitry configured to provide power to the circuitry.

27. The apparatus of claim 23, wherein the circuitry is configured to remove the noise from the ECG signals by:
identifying a location of a QRS complex of a cardiac cycle in the ECG signals;
identifying a first time window in the cardiac cycle that includes the QRS complex;
identifying a second time window in the cardiac cycle that does not include the QRS complex; and
removing a band of frequencies from the second time window.

28. The apparatus of claim 23, wherein the circuitry is configured to remove the noise from the ECG signals by:
decomposing the signal into subcomponents;
identifying a location of the QRS complex of a cardiac cycle in the ECG signal;
identifying a time window in the cardiac cycle that includes the QRS complex;
identifying a time window in the cardiac cycle that does not include the QRS complex;
for each of the time windows, identifying target ones of the subcomponents in the time window as subcomponents that contain more energy that is within a band of frequencies characteristic of a desired ECG signal in the time window than energy that is outside the band of frequencies characteristic of the desired ECG signal; and reconstructing a denoised signal using at least two of the identified target subcomponents.

* * * * *